(12) United States Patent
Poon et al.

(10) Patent No.: US 11,897,914 B2
(45) Date of Patent: Feb. 13, 2024

(54) SYNTHESIS OF 2' PROTECTED NUCLEOSIDES

(71) Applicant: Hongene Biotech Corporation, Union City, CA (US)

(72) Inventors: Wing C. Poon, Union City, CA (US); Ruiming Zou, Union City, CA (US); Aldrich N. K. Lau, Palo Alto, CA (US); David Yu, Union City, CA (US); Gengyu Du, Union City, CA (US); Yun-Chiao Yao, Union City, CA (US); Gang Zhao, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/059,357

(22) Filed: Nov. 28, 2022

(65) Prior Publication Data

US 2023/0416295 A1    Dec. 28, 2023

Related U.S. Application Data

(60) Provisional application No. 63/283,945, filed on Nov. 29, 2021.

(51) Int. Cl.
| | |
|---|---|
| *C07H 21/02* | (2006.01) |
| *C07H 19/10* | (2006.01) |
| *C07H 19/067* | (2006.01) |
| *C07H 19/167* | (2006.01) |
| *C07H 19/20* | (2006.01) |
| *C07H 23/00* | (2006.01) |

(52) U.S. Cl.
CPC ........... *C07H 21/02* (2013.01); *C07H 19/067* (2013.01); *C07H 19/10* (2013.01); *C07H 19/167* (2013.01); *C07H 19/20* (2013.01); *C07H 23/00* (2013.01)

(58) Field of Classification Search
CPC ...... C07H 21/02; C07H 19/067; C07H 19/10; C07H 19/167; C07H 19/20
See application file for complete search history.

(56) References Cited

U.S. PATENT DOCUMENTS

| | | |
|---|---|---|
| 5,808,035 A | 9/1998 | Usher et al. |
| 6,590,093 B1 | 7/2003 | Scaringe |
| 9,102,938 B2 | 8/2015 | Rajeev et al. |
| 9,249,175 B2 | 2/2016 | Damha et al. |
| 9,273,086 B2 | 3/2016 | Dellinger et al. |
| 2005/0267104 A1* | 12/2005 | Josyula ................ C07D 413/14 544/60 |

FOREIGN PATENT DOCUMENTS

| | | |
|---|---|---|
| WO | WO 96/18736 | 6/1996 |
| WO | WO 99/09044 | 2/1999 |
| WO | WO 08/090829 | 7/2008 |
| WO | WO 2009/144418 | 12/2009 |
| WO | WO 10/025566 | 3/2010 |
| WO | WO 13/027843 | 2/2013 |
| WO | WO 14/148928 | 9/2014 |
| WO | WO 16/159374 | 10/2016 |
| WO | WO 20/025566 | 2/2020 |

OTHER PUBLICATIONS

Martin et al., Bioorganic & Medicinal Chemistry Letters, 2009, 19, p. 4046-4049. (Year: 2009).*
Greene et al., Protective Groups in Organic Synthesis, 3rd Ed., 1999, p. 17-245. (Year: 1999).*
Carey, 1992, Organic Chemistry, 2d ed., McGraw-Hill, Inc., New York, pp. 328-331.
Greene et al., 1999, Protective Groups in Organic Synthesis, 3rd Ed., John Wiley & Sons, New York (TOC).
IUPAC-IUB Commission on Biochemical Nomenclatures, 1972, Abbreviated nomenclature of synthetic polypeptides (polymerized amino acids), revised recommendations (1971), Biochem. 11(5):942-944.
Johnsson et al., 2011, New light labile linker for solid phase synthesis of 2'-O-acetalester oligonucleotides and applications to siRNA prodrug development, Bioorganic & Medicinal Chemistry Letters, 21:3721-3725.
Lackey et al., 2009, Acetal levulinyl ester (ALE) groups for 2'-hydroxyl protection of ribonucleosides in the synthesis of oligoribonucleotides on glass and microarrays, J. Am. Chem. Soc., 131:8496-8502.
McMurry, 2000, Organic Chemistry, 5th ed., Brooks/Cole, Pacific Grove, CA, pp. 398 and 408.
McOmie, ed., 1973, Protective Groups in Organic Chemistry, Plenum Press (TOC).

(Continued)

*Primary Examiner* — Jonathan S Lau
(74) *Attorney, Agent, or Firm* — Knobbe, Martens, Olson & Bear LLP

(57) ABSTRACT

Embodiments of the present application relate to the preparation of 2'-O-protected nucleoside phosphoramidites and conjugation of the 2'-O-protected nucleoside to a solid support. More specifically, the present application relates to nucleosides having a hydroxy protecting group at the 2' position that reduces migration to the 3' position during RNA (e.g., mRNA) synthesis and can be readily removed under mild conditions without the use of toxic metal-containing reagents. Methods of using the nucleosides described herein in RNA synthesis are also disclosed.

23 Claims, 1 Drawing Sheet

Specification includes a Sequence Listing.

(56) References Cited

OTHER PUBLICATIONS

Scheit, 1980, Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Uhlman et al., Jun. 1990, Antisense oligonucleotides: a new therapeutic principle, Chemical Reviews, 90(4):543-584.
International Search Report and Written Opinion dated Feb. 24, 2023 in International Application No. PCT/US2022/080486.
Quaedflieg, et al., "An Alternative Approach towards the Synthesis of (3'->5') Methylene Acetal Linked Dinucleosides", Tetrahedron Letters, vol. 22, No. 21, pp. 3081-3084, 1992.

* cited by examiner

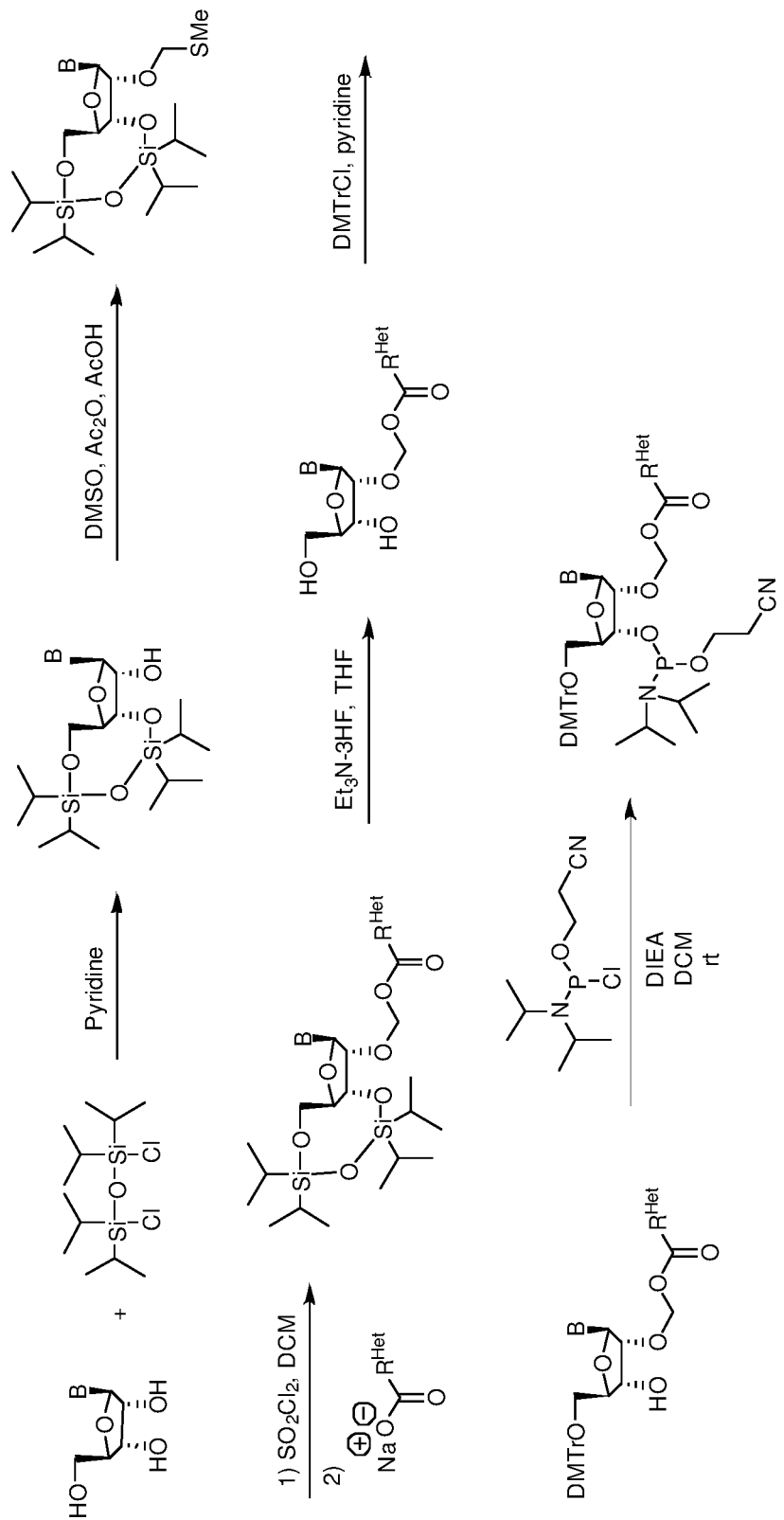

SEQUENCE LISTING

```
Sequence total quantity: 1
SEQ ID NO: 1            moltype = DNA   length = 10
FEATURE                 Location/Qualifiers
source                  1..10
                        mol_type = other DNA
                        organism = synthetic construct
SEQUENCE: 1
tttttttttt                                                          10
```

SYNTHESIS OF 2' PROTECTED NUCLEOSIDES

FIELD

The present application relates to 2' protected nucleosides, their methods of preparation, and their uses in oligonucleotide synthesis. More specifically, the present application relates to nucleoside phosphoramidites for use in RNA synthesis.

REFERENCE TO SEQUENCE LISTING

The present application is being filed along with a Sequence Listing in electronic format. The Sequence Listing is provided as a file entitled "HGENE.010A_Sequence_Listing.xml" created on Nov. 28, 2022, which is 1.89 KB in size. The information in the electronic format of the Sequence Listing is incorporated herein by reference in its entirety.

BACKGROUND

Description of the Related Art

Oligonucleotide-based drugs have become a powerful epitome having ability to treat various diseases. Due to the commercial availability of automated synthesizers, predetermined oligonucleotide sequences can be prepared rapidly and in large quantities using solid-phase synthesis. The preparation of stable nucleoside synthons such as phosphoramidites have been key factors in improving the efficiency of oligonucleotide synthesis.

A number of nucleoside phosphoramidites have been prepared and used in the process of RNA synthesis. Preparation of these phosphoramidites often require the use of a protecting group at the 2' position of the nucleoside phosphoramidites. Examples of 2' protecting group of nucleoside phosphoramidites include TBDMS (tert-butyldimethylsilyl) group, TOM (triisopropylsilyloxymethyl) group, ACE (bis (2-acetoxyethoxy)methyl) group, TC (thiomorpholine-4-carbothioate), EMM (cyanoethoxymethoxymethyl) and the like, for example, those disclosed in WO9618736, WO 99/09044, U.S. Pat. Nos. 6,590,093, 9,273,086, WO2008/090829, WO2013/027843, and WO2016/159374. Certain protecting groups may require several steps of synthesis and low final yields. Others may be difficult to remove using mild conditions and/or result in decreased efficiency or yield of oligonucleotide synthesis. Furthermore, a particular challenge faced during the synthesis of these phosphoramidite reagents is the migration of a protecting group at the 2' position to the 3' position of the nucleoside sugar moiety. Additionally, removal of protecting groups may require harsh or toxic conditions. For example, International Patent Publication No. WO 2014/148298 has previously reported the use of a —$CH_2OCH_2$Phenyl protecting group at the 2'-O atom of the ribose moiety. However, removal of this protecting group required the use of the highly toxic reagent tin (IV) chloride. As such, there exists a need to design and synthesis of 2' protected novel nucleoside phosphoramidites that obviate the need to use toxic and harsh deprotection conditions, but also with improved stability and reduce/stop 2' to 3' migration, and final may also improve the product yield.

SUMMARY

Some aspect of the present disclosure relates to a compound of Formula (I):

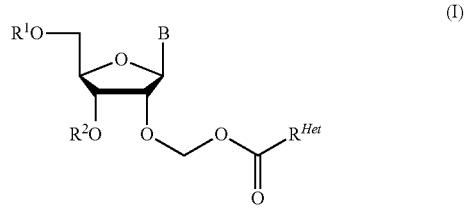

(I)

or a pharmaceutically acceptable salt thereof, wherein
$R^1$ is hydrogen or a hydroxy protecting group;
$R^2$ is hydrogen, a hydroxy protecting group, —C(=O)$CH_2CH_2C$(=O)$R^3$, or —P(O$R^4$)N$R^5R^6$;
alternatively, $R^1$ and $R^2$ are joined together to form a 6-10 membered heterocyclic ring;
$R^{Het}$ is optionally substituted 5-10 membered heteroaryl or optionally substituted 5-10 membered heterocyclyl;
$R^3$ is hydroxy, —O$R^7$ or —N$R^8R^9$;
each of $R^4$, $R^5$ and $R^6$ is independently H, unsubstituted $C_1$-$C_6$ alkyl, or substituted $C_1$-$C_6$alkyl;
$R^7$ is unsubstituted $C_1$-$C_6$ alkyl, substituted $C_1$-$C_6$ alkyl, or a hydroxy protecting group;
each of $R^8$ and $R^9$ is independently H, unsubstituted or substituted $C_{1-6}$ alkyl, or an amino protecting group; and
B is a natural nucleobase, a modified natural nucleobase, or an unnatural nucleobase.

In some embodiments of the compound of Formula (I), $R^1$ is a trityl type of hydroxy protecting group selected from (4-methoxyphenyl)diphenylmethyl, bis(4-methoxyphenyl) phenylmethyl, tris(4-methoxyphenyl)methyl, 9-phenylxanthen-9-yl, and 9-(4-methoxyphenyl)xanthen-9-yl. In one embodiment, $R^1$ is bis(4-methoxyphenyl)phenylmethyl. In other embodiments, $R^1$ is hydrogen.

In some embodiments of the compound of Formula (I), $R^2$ is hydrogen. In other embodiments, $R^2$ is a hydroxy protecting group.

In some embodiments of the compound of Formula (I), $R^2$ is —C(=O)$CH_2CH_2C$(=O)$R^3$, wherein $R^3$ is hydroxy, —O$R^7$ or —N$R^8R^9$. In some embodiments, $R^7$ is unsubstituted $C_1$-$C_6$ alkyl, substituted $C_1$-$C_6$ alkyl, or a hydroxy protecting group. In some embodiments, $R^7$ is unsubstituted $C_1$-$C_6$ alkyl, substituted $C_1$-$C_6$ alkyl, or a hydroxy protecting group. In one embodiment, $R^2$ is —C(=O)$CH_2CH_2C$(=O) OH. In another embodiment, $R^2$ is —C(=O)$CH_2CH_2C$(=O)$NH_2$.

In other embodiments of the compound of Formula (I), $R^2$ is —P(O$R^4$)N$R^5R^6$, wherein each of $R^4$, $R^5$ and $R^6$ is independently H, unsubstituted $C_1$-$C_6$ alkyl, or substituted $C_1$-$C_6$ alkyl. In some embodiments, $R^2$ is —P(O$R^4$)N$R^5R^6$, wherein $R^4$ is substituted $C_1$-$C_6$ alkyl and $R^5$ and $R^6$ are each independently unsubstituted $C_1$-$C_6$ alkyl. In some embodiments, $R^2$ is

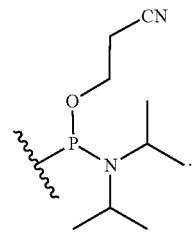 [SMILES: *P(OCCC#N)N(C(C)C)C(C)C]

In some embodiments of the compound of Formula (I), $R^1$ and $R^2$ are joined together to form a 6-10 membered heterocyclic ring. In some embodiments, $R^1$ and $R^2$ are joined together to form a 7 membered heterocyclic ring containing oxygen and silicon atoms. In some embodiments, the compound of Formula (I) is also represented by Formula (Ia):

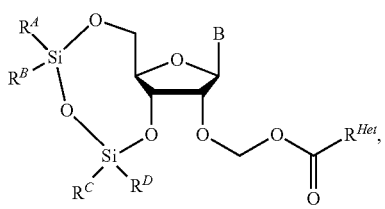
(Ia)

or a pharmaceutically acceptable salt thereof, wherein each of $R^A$, $R^B$, $R^C$, and $R^D$ is independently H, unsubstituted $C_1$-$C_6$ alkyl, or substituted $C_1$-$C_6$ alkyl. In certain embodiments, each of $R^A$, $R^B$, $R^C$, and $R^D$ is isopropyl.

In some embodiments of the compound of Formula (I), wherein $R^{Het}$ is optionally substituted 5-10 membered heteroaryl containing one to four heteroatoms selecting from the group consisting of O, N and S. In certain embodiments, $R^{Het}$ is selected from the group consisting of pyridinyl, pyrimidinyl, furanyl, pyrrolyl, thienyl, thiazolyl, isothiazolyl, imidazolyl, pyrazolyl, oxazolyl, isoxazolyl, benzofuranyl, benzoimidazolyl, benzopyrazolyl, benzothiazolyl, benzooxazolyl, indolyl, and quinolinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, $R^{Het}$ is 4-pyridinyl optionally substituted with one, two or three substituents Q. In other embodiments of the compound of Formula (I), $R^{Het}$ is optionally substituted 5-10 membered heterocyclyl containing one to four heteroatoms selecting from the group consisting of O, N and S. In certain embodiments, $R^{Het}$ is selected from the group consisting of tetrahydrofuranyl, tetrahydropyranyl, pyrrolidinyl, piperidinyl, piperazinyl, and morpholinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, each Q is independently selected from the group consisting of —F, —Cl, —Br, —CH$_3$, —CH$_2$CH$_3$, —CF$_3$, —CH$_3$, —OCH$_3$, and —OCH$_2$CH$_3$.

In some embodiments of the compound of Formula (I), B is:

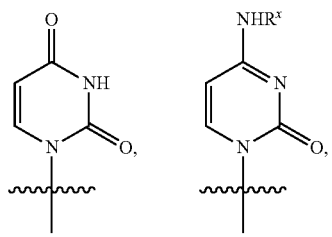

-continued

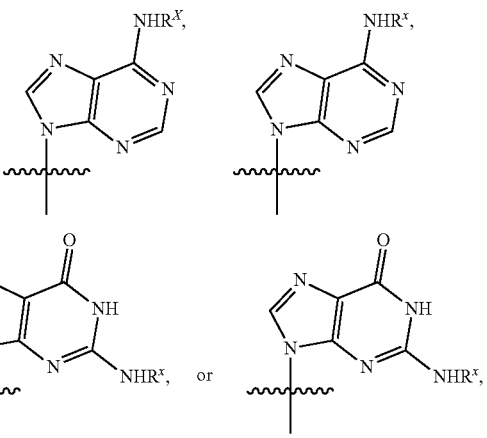

In some embodiments, wherein $R^x$ is hydrogen, $C_1$-$C_6$ alkyl, or an amino protecting group. In other embodiments, the hydrogen in —NHR$^x$ is absent, and $R^x$ is a divalent amino protecting group. For example, $R^x$ is

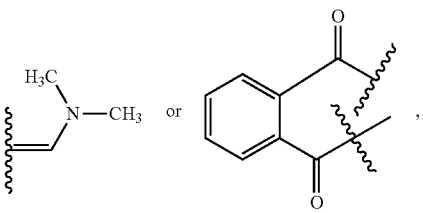

In some embodiments of the compound of Formula (I), the compound may include:

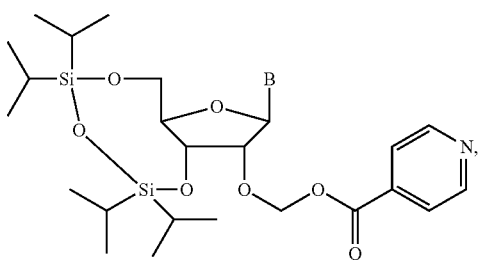

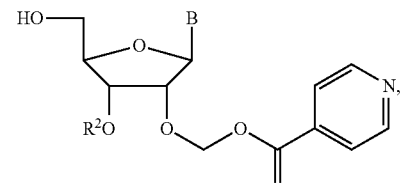

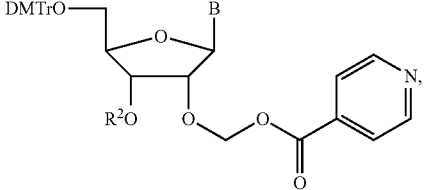

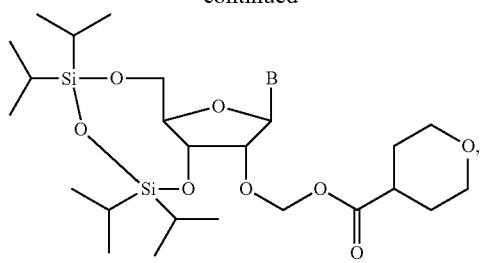
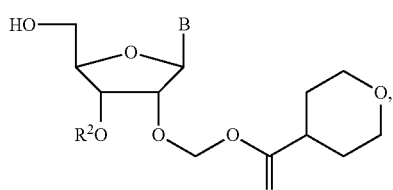
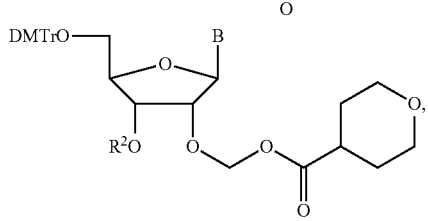
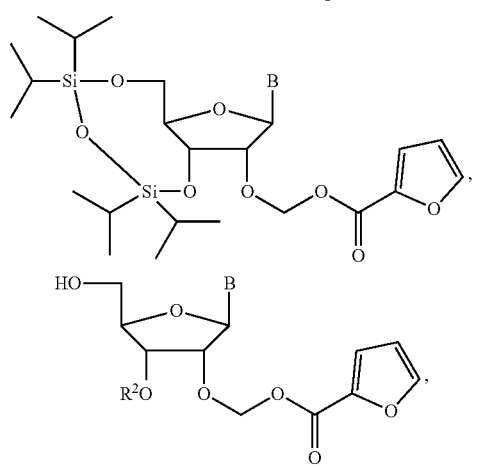
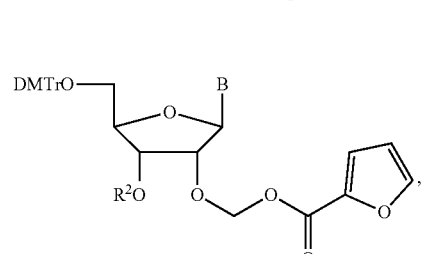
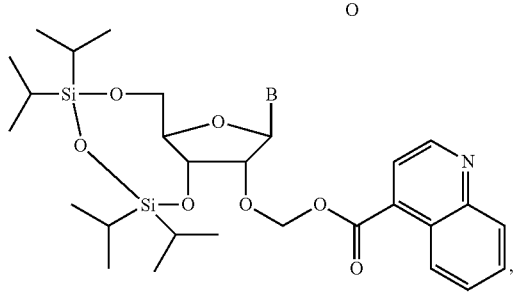
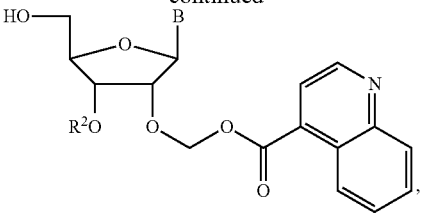
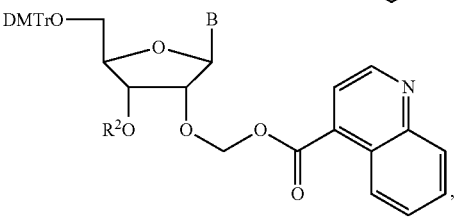
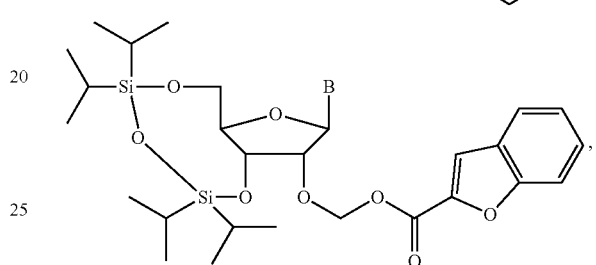
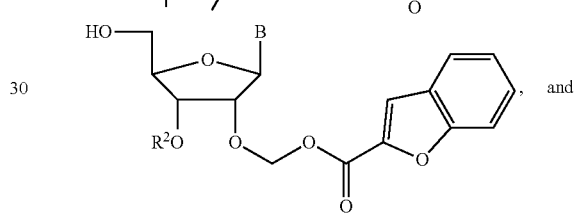
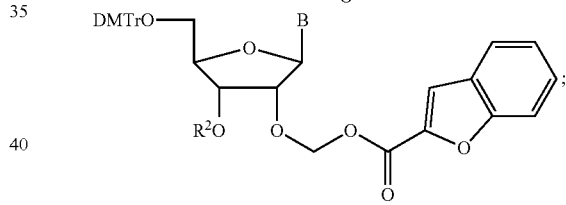
or salts thereof, wherein $R^2$ is H,
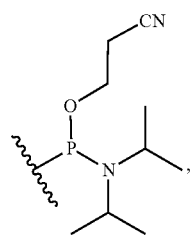 [SMILES: *P(OCCC#N)N(C(C)C)C(C)C]
—C(=O)CH$_2$CH$_2$C(O)OH or —C(=O)CH$_2$CH$_2$C(CO)NH$_2$; each
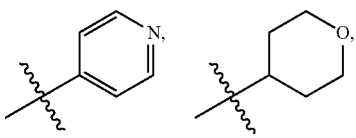 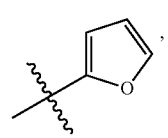

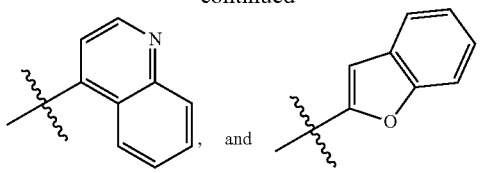

is optionally substituted with one substituent Q, wherein Q is selected from the group consisting of —F, —Cl, —Br, —CH$_3$, —CH$_2$CH$_3$, —CF$_3$, —CH$_3$, —OCH$_3$, and —OCH$_2$CH$_3$. In further embodiments, B is

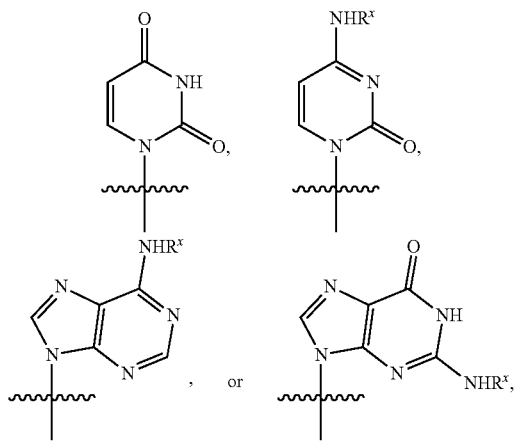

wherein R$^x$ is —C(=O)Ph (Bz), —C(=O)CH$_3$ (Ac) or —C(=O)CH(CH$_3$)$_2$ (iBu).

In another aspect of the present disclosure, disclosed herein is a method of preparing a synthetic oligonucleotide, comprising reacting a compound of Formula (I) as described herein with an oligonucleotide. In some embodiments, the oligonucleotide may have 1 to 100 nucleobase length. In some embodiments, the reaction may be conducted on a solid support, for example, CPG solid support.

In another aspect of the present disclosure, disclosed herein is a method of deprotecting an oligonucleotide or polynucleotide comprising at least one 2' protected nucleotide residue comprising the structure of Formula (II):

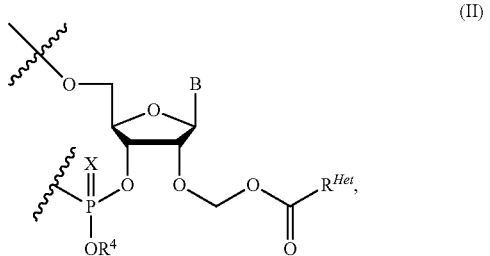

(II)

wherein
X is O or S;
R$^4$ is H, unsubstituted C$_1$-C$_6$ alkyl or substituted C$_1$-C$_6$ alkyl;
B is a natural nucleobase, a modified natural nucleobase, or an unnatural nucleobase; and
R$^{Het}$ is optionally substituted 5-10 membered heteroaryl or optionally substituted 5-10 membered heterocyclyl;

the method comprising: contacting the oligonucleotide or polynucleotide with a composition comprising an amine (e.g., a primary amine) or ammonia to deprotect the 2' protected nucleotide residue.

Further aspect of the present disclosure relates to oligonucleotide or polynucleotide prepared by the methods described herein.

Yet another aspect of the disclosure relates to a solid support bound oligonucleotide or polynucleotide comprising at least one 2' protected nucleotide residue comprising the structure of Formula (II):

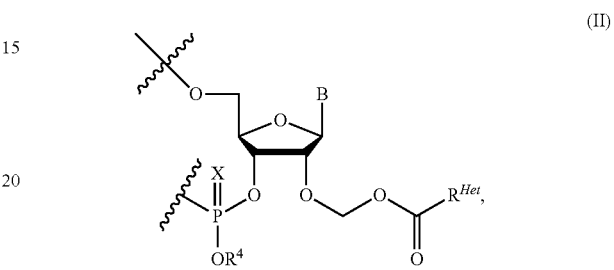

(II)

wherein
X is O or S;
R$^4$ is H, unsubstituted C$_1$-C$_6$ alkyl or substituted C$_1$-C$_6$ alkyl;
B is a natural nucleobase, a modified natural nucleobase, or an unnatural nucleobase; and
R$^{Het}$ is optionally substituted 5-10 membered heteroaryl or optionally substituted 5-10 membered heterocyclyl.

BRIEF DESCRIPTION OF THE DRAWINGS

FIG. 1 is a general reaction scheme for the preparation of a 2' nucleoside phosphoramidite wherein the —O-phosphoramidite is at the 3' position according to an embodiment of the present application.

DETAILED DESCRIPTION

The compounds disclosed herein relate to nucleoside phosphoramidites having a novel protecting group at the 2' position of the ribose moiety. In some embodiments, the 2' protected nucleoside phosphoramidite compounds disclosed herein may facilitate facile removal of the protection group without the use of harsh conditions or toxic metal reagents and also reduce/eliminate the undesired 2' to 3' migration of the protecting group. In some embodiments, the 2' protected nucleoside phosphoramidite compounds disclosed herein may be improve the yield and efficiency of RNA synthesis.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R_a$ and $R^b$, and the atom to which it is attached, are indicated to be "taken together" or "joined together" it means that they are covalently bonded to one another to form a ring:

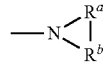

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (for example, $C_3$-$C_8$ cycloalkyl, $C_3$-$C_8$ cycloalkenyl, or $C_3$-$C_8$ cycloalkynyl, each may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy ($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); 5-10 membered heterocyclyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); aryl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$alkoxy)$C_1$-$C_6$ alkyl, or —O($C_1$-$C_6$ alkoxy)$C_1$-$C_6$ alkyl); 5-10 membered heteroaryl (may further be optionally substituted with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); (5-10 membered heteroaryl)$C_1$-$C_6$ alkyl (may further be optionally substituted with halo, $C_1$-$C_6$ alkyl, $C_1$-$C_6$ alkoxy, $C_1$-$C_6$ haloalkyl, $C_1$-$C_6$ haloalkoxy, hydroxy($C_1$-$C_6$ alkyl), ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy such as —$OCF_3$); ($C_1$-$C_6$ alkoxy) $C_1$-$C_6$ alkyl; —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro[3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered mono-cyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom, oxygen atom or sulfur atom). For example, a —$CH_2$— may be replaced with —O—, —S—, or —NH—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$— unit(s). Alternatively and/or additionally, one or more carbon atoms can also be substituted with an oxo (=O) to become a carbonyl. For example, a —$CH_2$— may be replaced with —C(=O)—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N($R_AR_B$)" group in which $R_A$ and $R_B$ can be the same as defined with respect to S-sulfonamido. An O-carbamyl may be substituted or unsubstituted.

An "N-carbamyl" group refers to an "ROC(=O)N($R_A$)—" group in which R and $R_A$ can be the same as defined with respect to N-sulfonamido. An N-carbamyl may be substituted or unsubstituted.

An "O-thiocarbamyl" group refers to a "—OC(=S)—N($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(=S)N($R_A$)—" group in which R and $R_A$ can be the same as defined with respect to N-sulfonamido. An N-thiocarbamyl may be substituted or unsubstituted.

A "C-amido" group refers to a "—C(=O)N($R_AR_B$)" group in which $R_A$ and $R_B$ can be the same as defined with respect to S-sulfonamido. A C-amido may be substituted or unsubstituted.

An "N-amido" group refers to a "RC(=O)N($R_A$)—" group in which R and $R_A$ can be the same as defined with respect to N-sulfonamido. An N-amido may be substituted or unsubstituted.

Where the numbers of substituents is not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

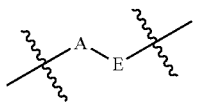

includes the substituent being oriented such that the A is attached at the leftmost attachment point of the molecule as well as the case in which A is attached at the rightmost attachment point of the molecule. In addition, if a group or substituent is depicted as

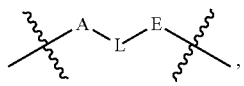

and when L is defined as a bond or absent; such group or substituent is equivalent to

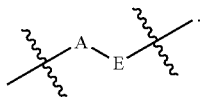

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4''-trimethoxytrityl (TMTr)).

Examples of hydroxy protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl) xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of protecting groups commonly used to protect phosphate and phosphorus hydroxy groups include without limitation, methyl, ethyl, benzyl (Bn), phenyl, isopropyl, tert-butyl, allyl, cyclohexyl (cHex), pivaloyloxymethyl (—CH$_2$—O—C(=O)C(CH$_3$)$_3$, or POM), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio) ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino)

butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl, 2-cyanoethyl and POM.

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxy group that is present in ribose. The nitrogen containing heterocyclic base can be purine or pyrimidine base. Purine bases include adenine (A) and guanine (G), and modified derivatives or analogs thereof, such as deazapurine or 7-deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

A "nucleotide residue" is a nucleotide that is a single residue of a polynucleotide. A nucleotide monomer once incorporated into a polynucleotide, becomes a nucleotide residue. A terminal nucleotide residue of a polynucleotide may be bound to a solid support indirectly via the other end of the polynucleotide of which it is a part, e.g., via a linker, or it may be bound to a solid support directly, e.g., when it is the first nucleotide residue of the oligonucleotide chain, as for example can be done in the synthesis of an array.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog"

as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

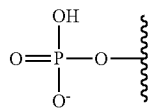

and

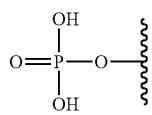

). As used herein, the terms "monophosphate," "diphosphate," and "triphosphate" are used in their ordinary sense as understood by those skilled in the art, and include protonated forms. In addition, oligonucleotide or polynucleotide as described herein, which contains one or more phosphodiester linkage, each phosphodiester linkage includes both protonated form, for example,

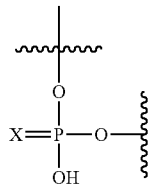

(wherein X is O or S), and unprotonated form

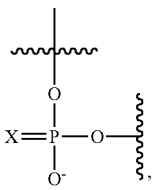

or a salt form.

2' Protected Nucleosides of Formula (I)

Some embodiments provide a compound of Formula (I), or a pharmaceutically acceptable salt thereof as described herein:

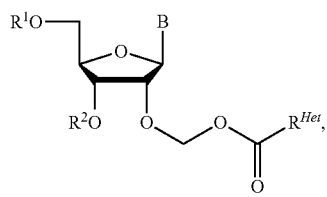

or a pharmaceutically acceptable salt thereof.

In some embodiments of the compounds of Formula (I), $R^1$ is hydrogen or a hydroxy protecting group. In some embodiments, $R^1$ is hydrogen. In other embodiments, $R^1$ is a trityl type of hydroxy protecting selected from (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In some specific embodiments, $R^1$ is bis(4-methoxyphenyl)phenylmethyl. In other embodiments, $—OR^1$ is a mono-, di- or tri-phosphate.

In some embodiments of the compounds of Formula (I), $R^2$ is hydrogen, a hydroxy protecting group, $—C(=O)CH_2CH_2C(=O)R^3$, or $—P(OR^4)NR^5R^6$. In some embodiments, $R^2$ is hydrogen. In other embodiments, $R^2$ is a hydroxy protecting group. In some embodiments, $R^2$ is $—C(=O)CH_2CH_2C(=O)R^3$, wherein $R^3$ is $—OH$, $—OR^7$ or $—NR^8R^9$. In some embodiments, $R^7$ is unsubstituted $C_1$-$C_6$ alkyl, substituted $C_1$-$C_6$ alkyl, or a hydroxy protecting group. In some embodiments, each of $R^8$ and $R^9$ is independently H, optionally substituted $C_{1-6}$ alkyl or an amino protecting group. In one embodiment, $R^2$ is $—C(=O)CH_2CH_2C(=O)OH$. In other embodiments, $R^2$ is $—P(OR^4)NR^5R^6$, wherein each of $R^4$, $R^5$ and $R^6$ is independently H, unsubstituted $C_{1-6}$ alkyl, or substituted $C_{1-6}$ alkyl. In some embodiments, $R^2$ is $—P(OR^4)NR^5R^6$, wherein $R^4$ is substituted $C_{1-6}$ alkyl and $R^5$ and $R^6$ are each independently unsubstituted $C_1$-$C_6$ alkyl. In other embodiments, $R^4$ is unsubstituted $C_{1-6}$ alkyl such as methyl, ethyl, isopropyl. In one embodiment, $R^2$ is

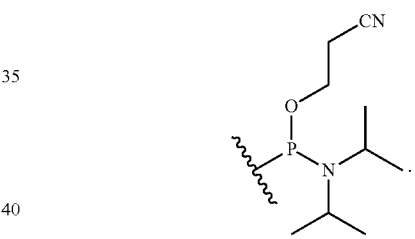

In some other embodiments of the compounds of Formula (I), $R^1$ and $R^2$ are joined together to form a 6-10 membered heterocyclic ring. In some embodiments, $R^1$ and $R^2$ are joined together to form a 7 membered heterocyclic ring containing oxygen and silicon atoms, for example, the compounds have the structure of Formula (Ia):

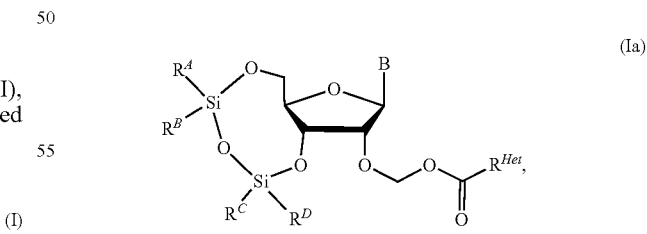

or a pharmaceutically acceptable salt thereof. In some embodiments, each of $R^A$, $R^B$, $R^C$, and $R^D$ is independently H, unsubstituted $C_1$-$C_6$ alkyl, or substituted $C_1$-$C_6$ alkyl. In some specific embodiments, each of $R^A$, $R^B$, $R^C$, and $R^D$ is isopropyl, In some embodiments of the compounds of Formula (I) or (Ia), $R^{Het}$ is optionally substituted 5-10 membered heteroaryl containing one to four heteroatoms selecting from the group consisting of O, N and S. In some further embodiments, $R^{Het}$ is selected from the group consisting of pyridinyl, pyrimidinyl, furanyl, pyrrolyl, thienyl, thiazolyl, isothiazolyl, imidazolyl, pyrazolyl, oxazolyl, isoxazolyl, benzofuranyl, benzoimidazolyl, benzopyrazolyl, benzothiazolyl, benzooxazolyl, indolyl, and quinolinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, $R^{Het}$ is 4-pyridinyl optionally substituted with one, two or three substituents Q. In some embodiments, $R^{Het}$ is 4-pyridinyl optionally substituted with one, two or three substituents Q, wherein each Q is independently selected from the group consisting of —F, —Cl, —Br, —$CH_3$, —$CH_2CH_3$, —$CF_3$, —$CH_3$, —$OCH_3$, and —$OCH_2CH_3$.

In some other embodiments of the compounds of Formula (I) or (Ia), $R^{Het}$ is optionally substituted 5-10 membered heterocyclyl containing one to four heteroatoms selecting from the group consisting of O, N and S. In further embodiments, $R^{Het}$ is selected from the group consisting of tetrahydrofuranyl, tetrahydropyranyl, pyrrolidinyl, piperidinyl, piperazinyl, and morpholinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, each Q is independently selected from the group consisting of —F, —Cl, —Br, —$CH_3$, —$CH_2CH_3$, —$CF_3$, —$CH_3$, —$OCH_3$, and —$OCH_2CH_3$.

In some embodiments of the compounds of Formula (I) or (Ia), B is a natural nucleobase. In other embodiments, B is a modified natural nucleobase. In yet other embodiments, B is an unnatural nucleobase. In some embodiments, B is

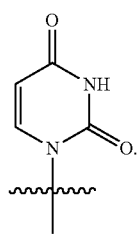 [SMILES: *n1ccc(=O)[nH]c1=O]

In other embodiments, B is

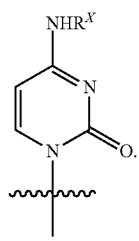

In other embodiments, B is

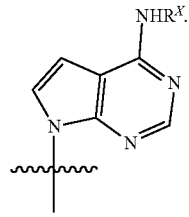

In yet other embodiments, B is

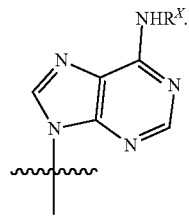

In still yet other embodiments, B is

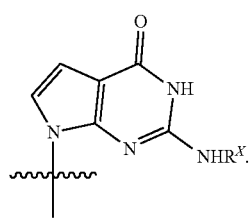

In some embodiments, B is

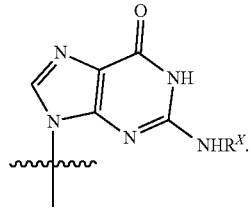

In some embodiments, $R^x$ is hydrogen, $C_1$-$C_6$ alkyl (such as methyl, ethyl, isopropyl, n-butyl, t-butyl), or an amino protecting group. In one embodiment, $R^x$ is methyl. In other embodiments, the hydrogen in —$NHR^x$ is absent, and $R^x$ is a divalent amino protecting group. In some embodiments, $R^x$ is —C(=O)$C_{1-6}$alkyl. For example, in some embodiments, $R^x$ is —C(=O)$CH_3$ (Ac), —C(=O)$CH_2CH_3$, or —C(=O)CH($CH_3$)$_2$ (iBu). In other embodiments, $R^x$ is —C(=O)-phenyl. In some other embodiments, the hydrogen in —$NHR^x$ is absent, and $R^x$ directed attaches to the nitrogen atom form an amino protecting group such as amidine type protecting group or the phthaloyl type protecting group. In some such embodiments, $R^x$ is N,N,-dimethylformamidine

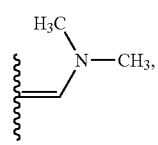
In some other embodiments, $R^x$ is
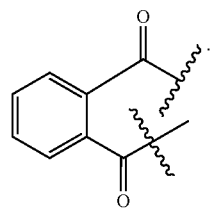 [SMILES: *C(=O)c1ccccc1C(*)=O]
Additional non-limiting examples of the compounds of Formula (I) include:
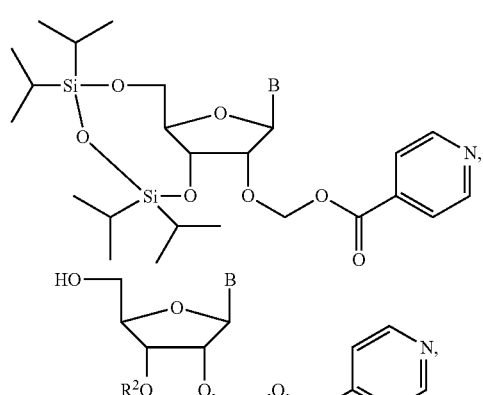
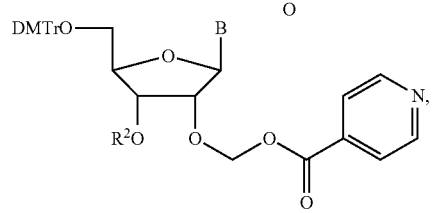
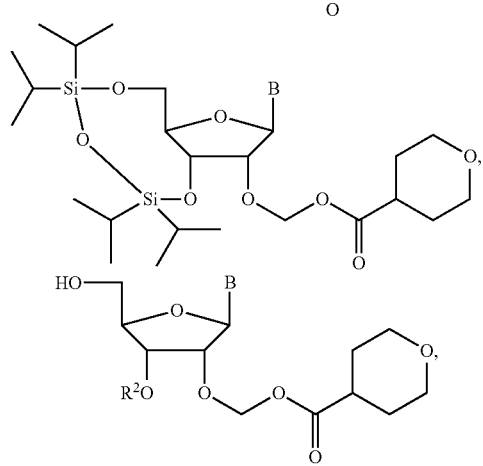
-continued
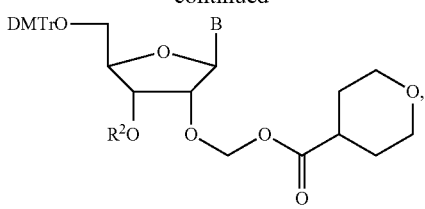
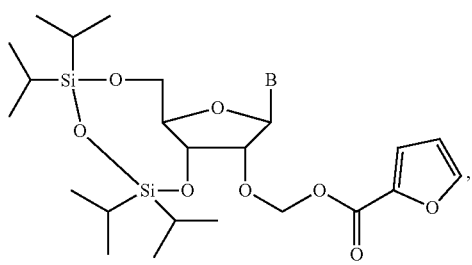
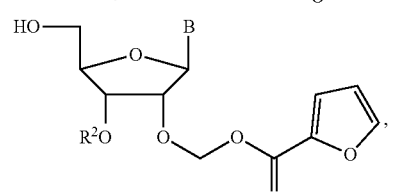
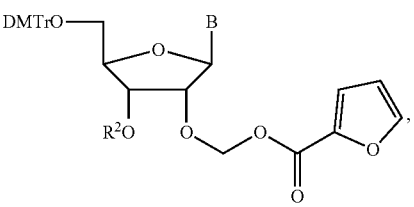
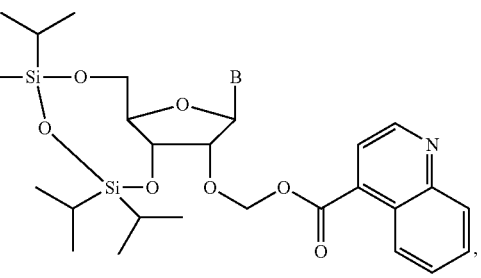
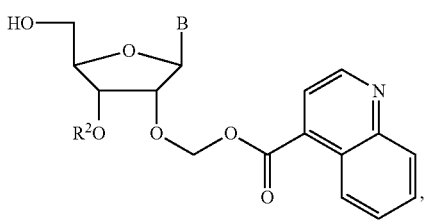
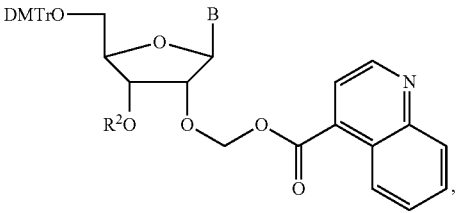

27
-continued
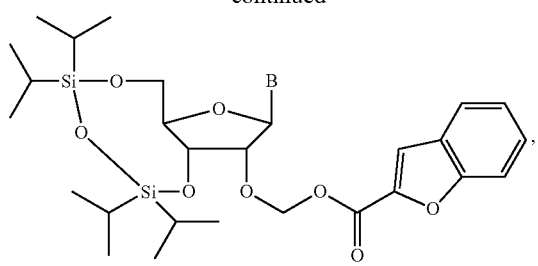
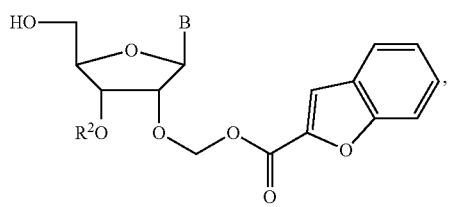
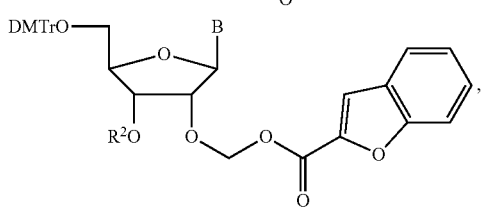
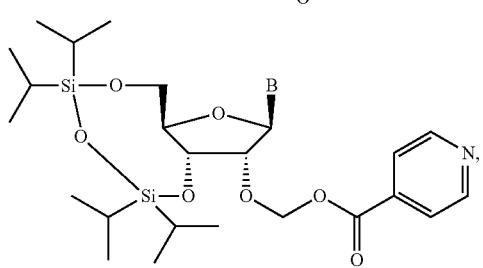
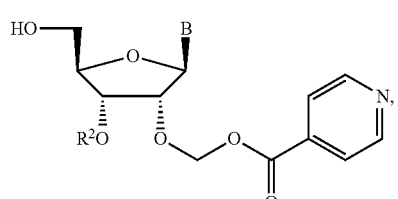
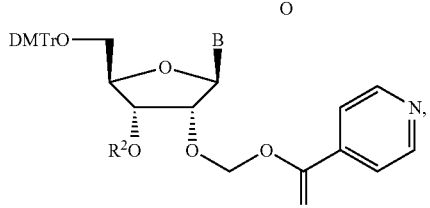
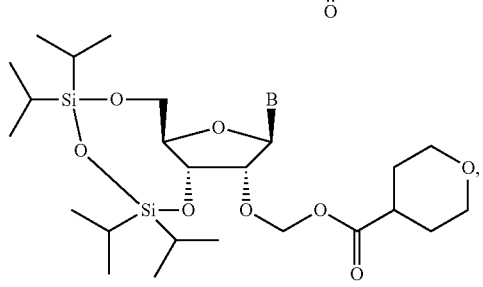
28
-continued
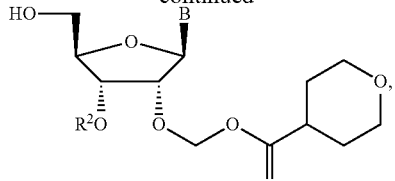
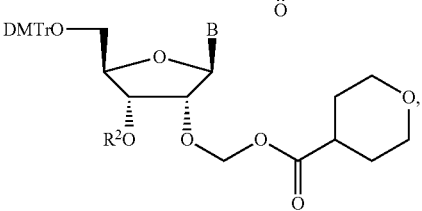
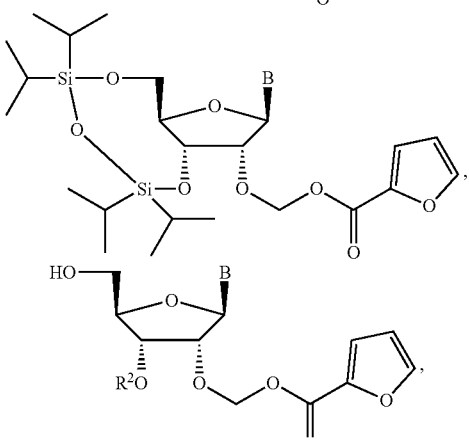
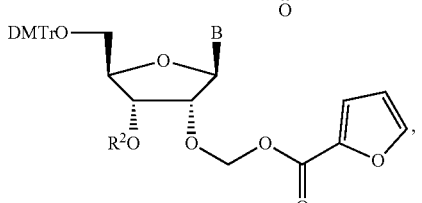
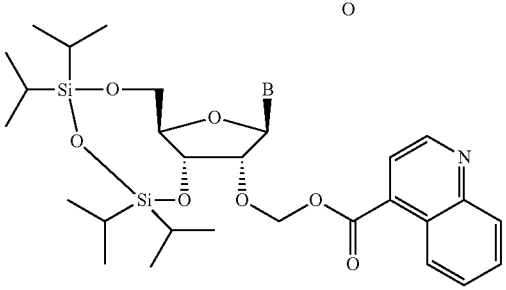
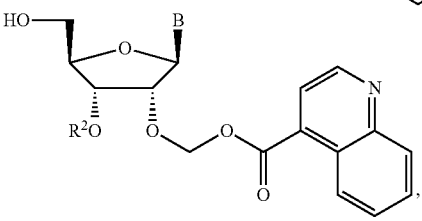
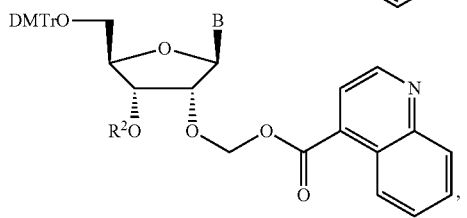

-continued

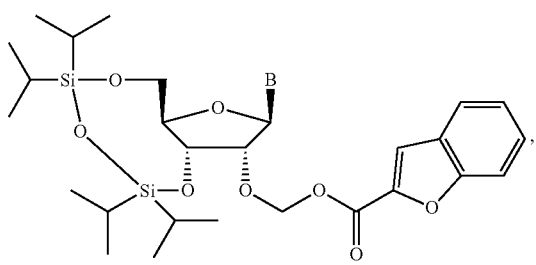

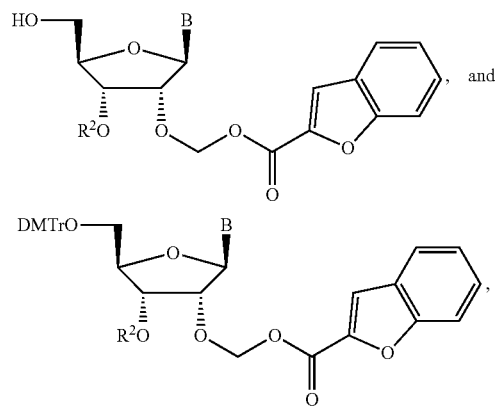

and salts thereof; wherein R² is H,

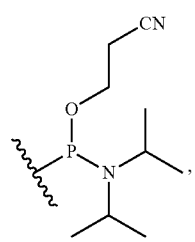 [SMILES: *P(OCCC#N)N(C(C)C)C(C)C]

—C(=O)CH₂CH₂C(=O)OH or —C(=O)CH₂CH₂C(=O)NH₂, each

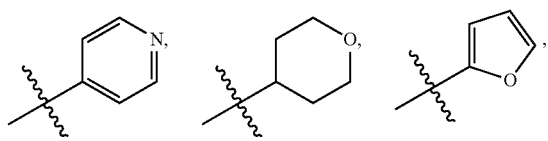

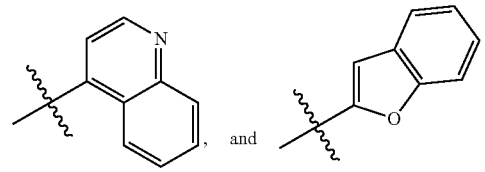

is optionally substituted with one substituent Q, wherein Q is selected from the group consisting of —F, —Cl, —Br, —CH₃, —CH₂CH₃, —CF₃, —CH₃, —OCH₃, and —OCH₂CH₃; and wherein B is a natural nucleobase, a modified natural nucleobase, or an unnatural nucleobase as described herein. In some embodiments, R² is

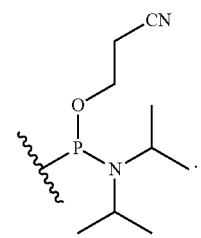 [SMILES: *P(OCCC#N)N(C(C)C)C(C)C]

In some further embodiments, B is

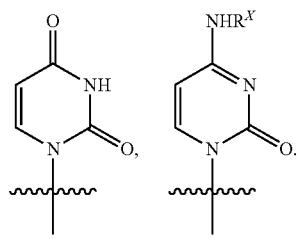

In still further embodiments, $R^x$ is —C(=O)Ph (Bz), —C(=O)CH₃ (Ac) or —C(=O)CH(CH₃)₂ (iBu).

Additional non-limiting examples of the compounds of Formula (I) include:

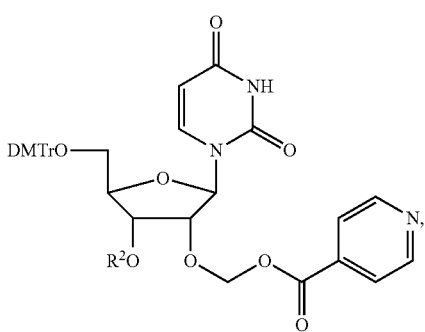

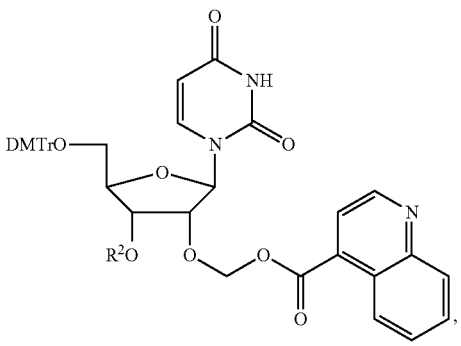

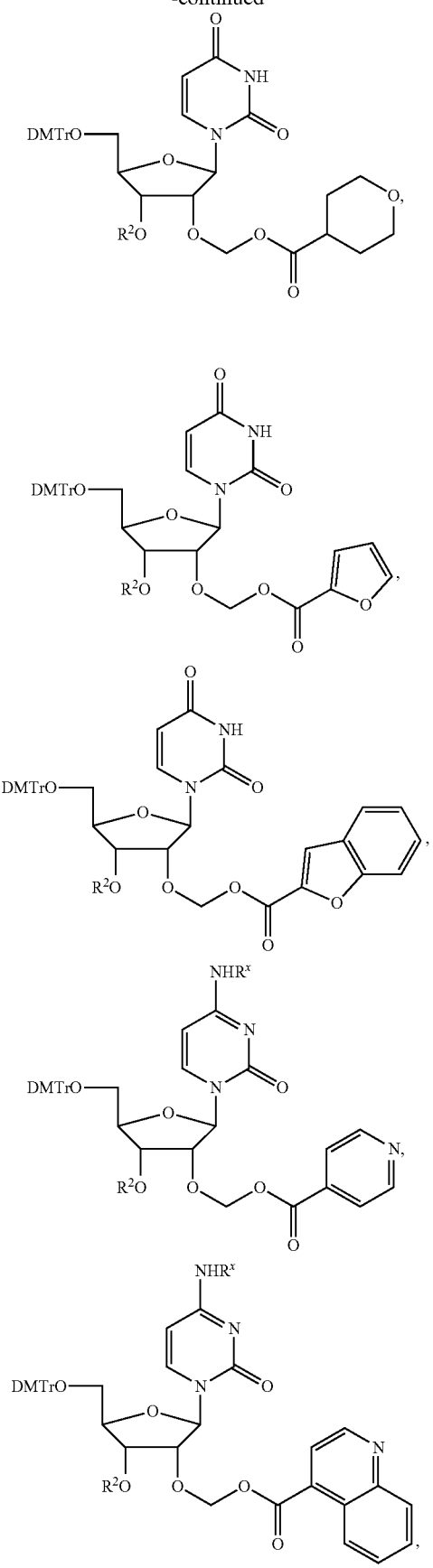
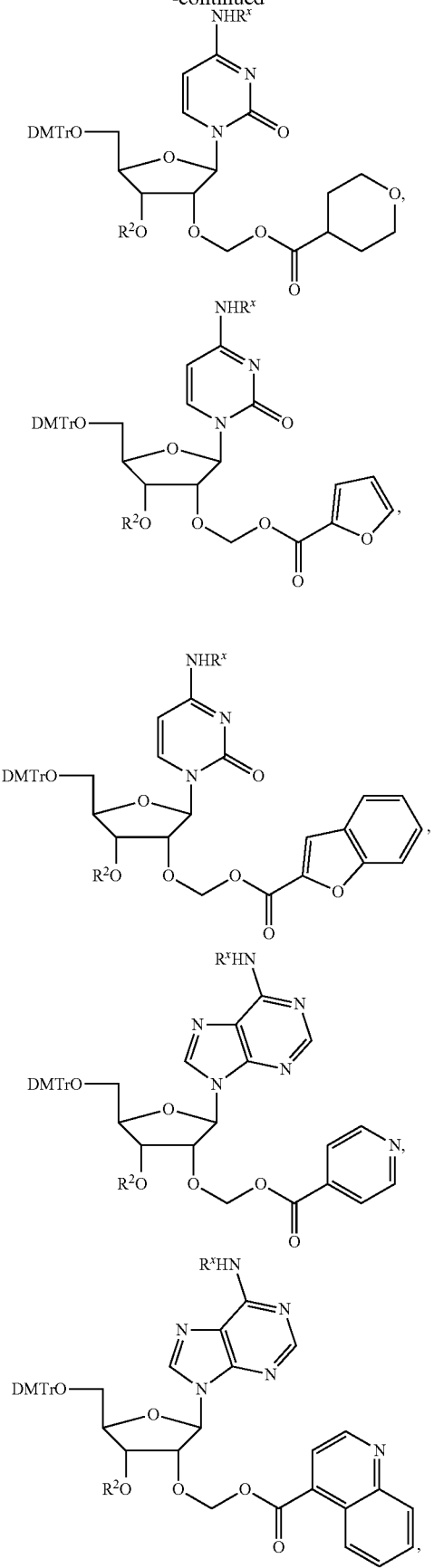

33
-continued

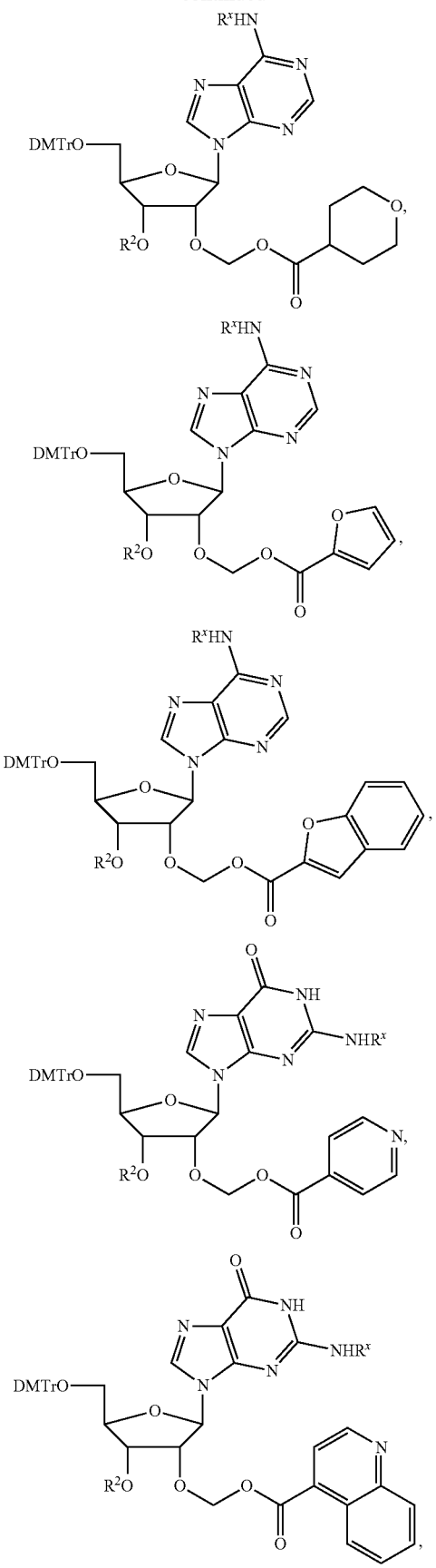

34
-continued

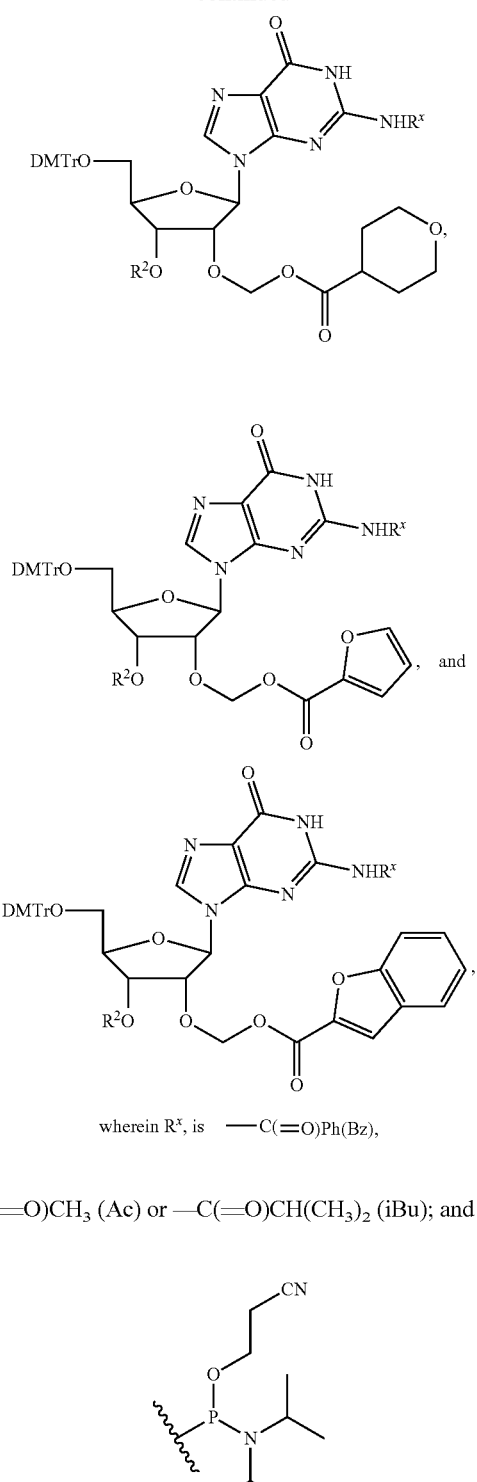

wherein $R^x$, is —C(=O)Ph(Bz),
—C(=O)CH₃ (Ac) or —C(=O)CH(CH₃)₂ (iBu); and $R^2$ is

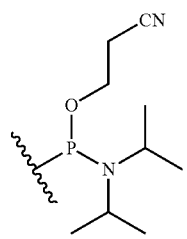 [SMILES: *P(OCCC#N)N(C(C)C)C(C)C]

or —C(=O)CH₂CH₂C(=O)OH.

In any embodiments of the compound of Formula (I) or (Ia) as described herein, the compound can be covalently attached to a solid support via $R^2$ of the compound. For example, when $R^2$ is —C(=O)CH₂CH₂C(=O)OH, the compound can be covalently attached to the solid support via a moiety:

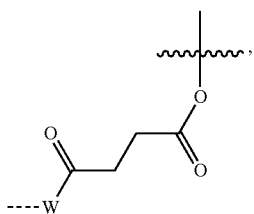

wherein W is O or NH;
wherein the dashed line refers to the connection with the solid support, optionally through an additional linker, and wherein the squiggly line refers to the point of the attachment of the oxygen atom that covalently attached to $R^2$ of the compound, to the remaining portion of the compound. In some embodiments, the solid support is a controlled pore glass (CPG) solid support.

Removal of the 2' Protecting Group

Some embodiments of the present disclosure relate to a method of deprotecting an oligonucleotide or polynucleotide comprising at least one 2' protected nucleotide residue comprising the structure of Formula (II):

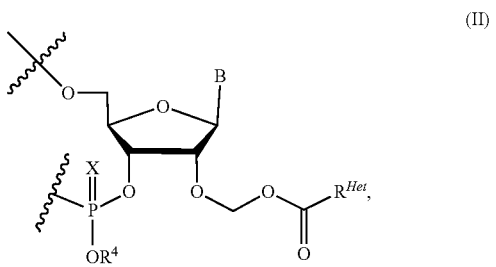

the method comprising contacting the oligonucleotide or polynucleotide with a composition comprising an amine (e.g., a primary amine) or ammonia to deprotect the 2' protected nucleotide residue.

In some embodiments of the deprotection method described herein, the 2' protecting group of the nucleotide residue may be removed in the presence of one or more amines in a solvent, for example a solvent containing alcohol. In some such embodiments, the amine may be a primary amine, a secondary amine or a tertiary amine, or combinations thereof. In one embodiment, the 2' protecting group may be removed by treatment with ammonia in methanol. In other embodiments, the 2' protecting group may be removed by treatment with n-butylamine in methanol.

In some embodiment of the deprotection method described herein, $R^4$ is H. In other embodiments, $R^4$ is unsubstituted $C_1$-$C_6$ alkyl or substituted $C_1$-$C_6$ alkyl. In one such embodiment, $R^4$ is —$CH_2CH_2CN$. In another embodiment, $R^4$ is methyl. In another embodiment, $R^4$ is ethyl. When

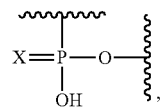

moiety of Formula (II) is

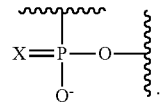

the compound also exists in unprotonated form $$X=\overset{\cdot}{\underset{O^-}{P}}-O-$$

In some embodiments, X is O or S. In some further embodiments, X is O. In some embodiments, B is a natural nucleobase. In other embodiments, B is a modified natural nucleobase. In yet other embodiments, B is an unnatural nucleobase. In some embodiments, B is

[uracil structure]

In other embodiments, B is

[cytosine structure with NHR^X]

In other embodiments, B is

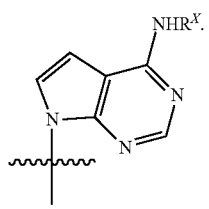

In yet other embodiments, B is

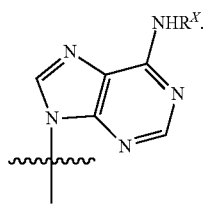

In still yet other embodiments, B is

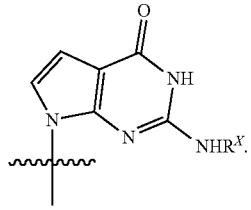

In some embodiments, B is

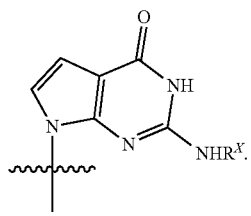

In some embodiments, $R^x$ is hydrogen, $C_1$-$C_6$ alkyl (such as methyl, ethyl, isopropyl, n-butyl, t-butyl), or an amino protecting group. In one embodiment, $R^x$ is methyl. In other embodiments, the hydrogen in —$NHR^x$ is absent, and $R^x$ is a divalent amino protecting group. In some embodiments, $R^x$ is —C(=O)$C_{1-6}$ alkyl. For example, in some embodiments, $R^x$ is —C(=O)$CH_3$ (Ac), —C(=O)$CH_2CH_3$, or —C(=O)CH($CH_3$)$_2$ (iBu). In other embodiments, $R^x$ is —C(=O) phenyl. In some other embodiments, the hydrogen in —$NHR^x$ is absent, and $R^x$ directed attaches to the nitrogen atom form an amino protecting group such as amidine type protecting group or the phthaloyl type protecting group. In some such embodiments, $R^x$ is N,N,-dimethylformamidine

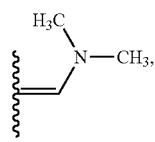 [SMILES: *=CN(C)C]

In some other embodiments, $R^x$ is

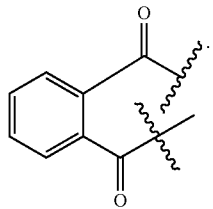 [SMILES: *C(=O)c1ccccc1C(*)=O]

In some embodiment of the deprotection method described herein, $R^{Het}$ is optionally substituted 5-10 membered heteroaryl or optionally substituted 5-10 membered heterocyclyl. In further embodiments, $R^{Het}$ is optionally substituted 5-10 membered heteroaryl containing one to four heteroatoms selecting from the group consisting of O, N and S. In some such embodiments, $R^{Het}$ is selected from the group consisting of pyridinyl, pyrimidinyl, furanyl, pyrrolyl, thienyl, thiazolyl, isothiazolyl, imidazolyl, pyrazolyl, oxazolyl, isoxazolyl, benzofuranyl, benzoimidazolyl, benzopyrazolyl, benzothiazolyl, benzooxazolyl, indolyl, and quinolinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, $R^{Het}$ is 4-pyridinyl optionally substituted with one, two or three substituents Q. In some embodiments, $R^{Het}$ is 4-pyridinyl optionally substituted with one, two or three substituents Q, wherein each Q is independently selected from the group consisting of —F, —Cl, —Br, —$CH_3$, —$CH_2CH_3$, —$CF_3$, —$CH_3$, —$OCH_3$, and —$OCH_2CH_3$.

In some other embodiment of the deprotection method described herein, optionally substituted 5-10 membered heterocyclyl containing one to four heteroatoms selecting from the group consisting of O, N and S. In further embodiments, $R^{Het}$ is selected from the group consisting of tetrahydofuranyl, tetrahydropyranyl, pyrrolidinyl, piperidinyl, piperazinyl, and morpholinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, each Q is independently selected from the group consisting of —F, —Cl, —Br, —$CH_3$, —$CH_2CH_3$, —$CF_3$, —$CH_3$, —$OCH_3$, and —$OCH_2CH_3$.

In some further embodiments of the deprotection method, the 2' nucleotide residue is selected from the group consisting of:

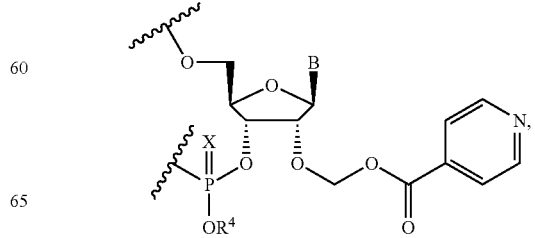

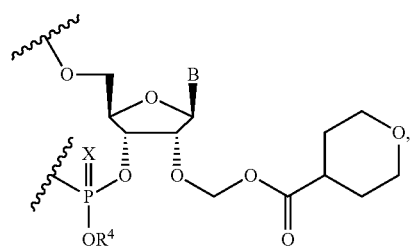
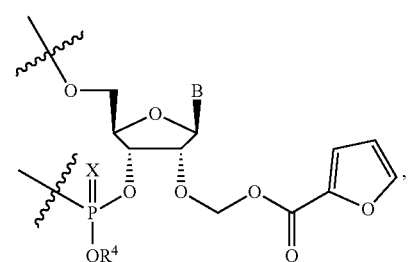
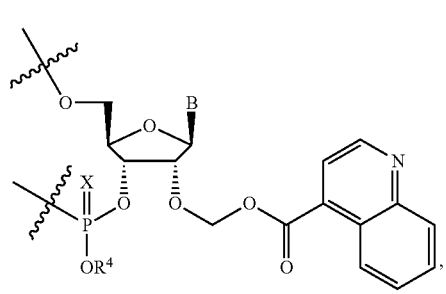
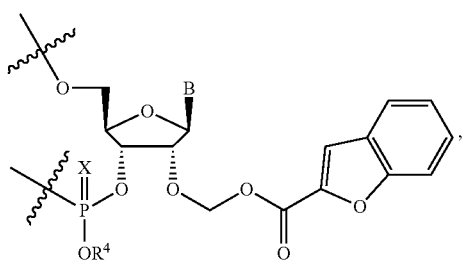
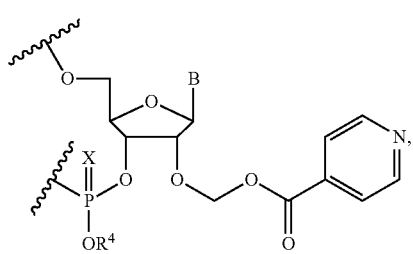
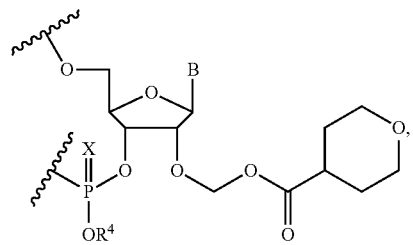
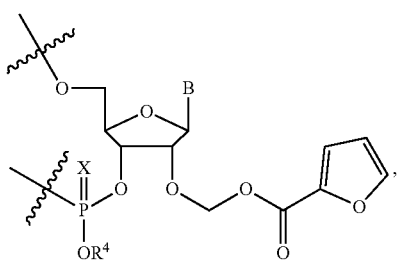
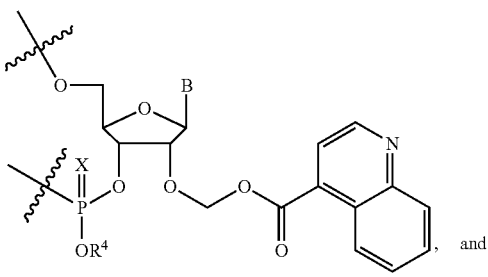
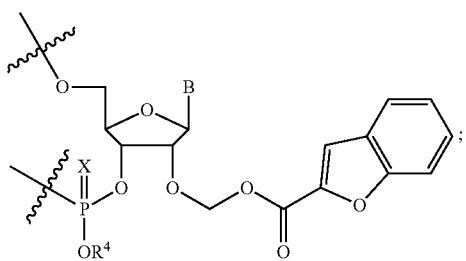
wherein R⁴ is H, methyl, ethyl, or —CH₂CH₂CN; each
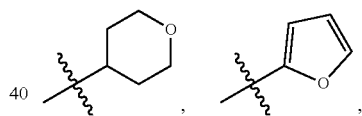
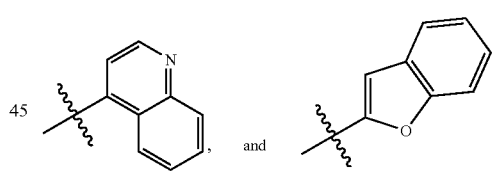
is optionally substituted with one to three substituent Q, and wherein each Q is independently selected from the group consisting of —F, —Cl, —Br, —CH₃, —CH₂CH₃, —CF₃, —CH₃, —OCH₃, and —OCH₂CH₃; and B is as described. In further embodiments, X is O. In further embodiments, B is
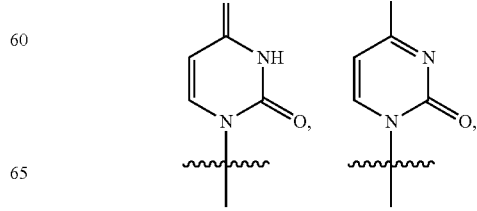

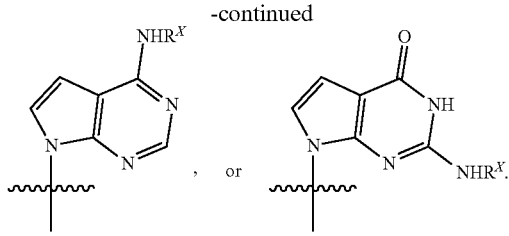

In further embodiments, $R^x$ is —C(=O)Ph (Bz), —C(=O)CH$_3$ (Ac) or —C(=O)CH(CH$_3$)$_2$ (iBu).

In some further embodiments of the deprotection method, the oligonucleotide or polynucleotide is bound to a solid support.

Some additional embodiments of the present disclosure relate to an oligonucleotide or polynucleotide prepared by the 2' deprotection method described herein.

Additional embodiments of the present disclosure relate to a method of deprotecting a solid support bound oligonucleotide or polynucleotide comprising a phosphate protecting group, a nucleobase protecting group (e.g., $R^4$); and a nucleotide residue comprising 2'-protecting group having the structure of Formula (II) as described herein. In certain embodiments the method comprises:
  (a) contacting the oligonucleotide or polynucleotide with a first composition comprising a phosphate deprotection reagent, under conditions sufficient to remove the phosphate protecting group and produce a first deprotected polynucleotide;
  (b) contacting the first deprotected polynucleotide with a second composition comprising a 2'deprotection reagent as described herein under conditions sufficient to remove the 2' protecting group and produce a second deprotected polynucleotide; and
  (c) contacting the second deprotected polynucleotide with a third composition comprising a diamine, under conditions sufficient to remove the nucleobase protecting group and produce a fully deprotected polynucleotide.

In some embodiments, any of the two or three of the steps (a)-(c) may be done under the same condition or simultaneously. In further embodiments, the method is a one-pot reaction.

In further embodiments, the method described herein produces a cleaved polynucleotide; wherein the cleaved polynucleotide is retained on the solid support. The method may further comprise washing the solid support and cleaved polynucleotide; and eluting the cleaved polynucleotide from the solid support.

In certain embodiments retention of the cleaved polynucleotide on the solid support allows for the cleaved polynucleotide to be easily separated from the composition and the deprotected protecting group products, for example by one or more wash steps. The composition may also be removed from the cleaved polynucleotide by a drying, evaporation, vacuum step, or the like.

2' Protected Nucleoside Phosphoramidites in RNA Synthesis

Some embodiments of the present application relate to a process for preparing a synthetic oligonucleotide, comprising reacting a compound of Formula (I) as described herein, with an oligonucleotide. In some embodiments, the oligonucleotide comprises 1 to 100 base length, 5 to 50 base length, or 10 to 30 base length. In further embodiments, the reaction is conducted on a solid support. In particular, the compound of Formula (I) contains a 3' phosphoramidite group (i.e., $R^2$ is —P(OR$^4$)NR$^5$R$^6$. In further embodiment, $R^2$ is

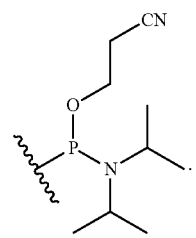 [SMILES: *P(OCCC#N)N(C(C)C)C(C)C]

For example, the compound of Formula (I) as described herein may react with an unprotected hydroxy group of the oligonucleotide or polynucleotide (e.g., 5' terminal hydroxy of the oligonucleotide or polynucleotide).

Additional embodiments of the present disclosure relate to an oligonucleotide or polynucleotide prepared by the synthetic process described herein.

In particular, certain embodiments relate to a solid support bound oligonucleotide or polynucleotide comprising at least one 2' protected ribonucleotide residue comprising the structure of Formula (II):

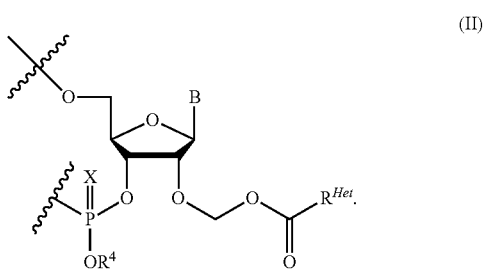

(II)

In some embodiment of the surface bound oligonucleotide or polynucleotide described herein, $R^4$ is unsubstituted $C_1$-$C_6$ alkyl or substituted $C_1$-$C_6$ alkyl. In one such embodiment, $R^4$ is —CH$_2$CH$_2$CN. In other embodiments, $R^4$ is methyl or ethyl. In another embodiment, $R^4$ is H. When

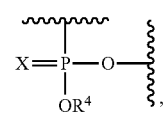

moiety of Formula (II) is

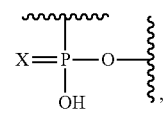

the compound also exists in unprotonated form

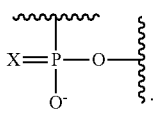

In some embodiments, X is O or S. In some further embodiments, X is O. In some embodiments, B is a natural nucleobase. In other embodiments, B is a modified natural nucleobase. In yet other embodiments, B is an unnatural nucleobase. In some embodiments, B is

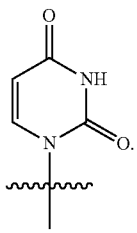 [SMILES: *n1ccc(=O)[nH]c1=O]

In other embodiments, B is

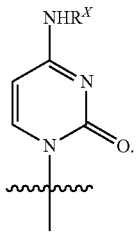

In other embodiments, B is

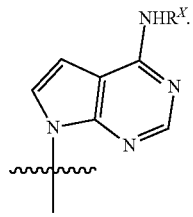

In yet other embodiments, B is

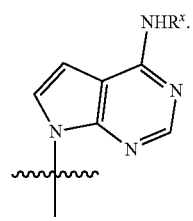

In still yet other embodiments, B is

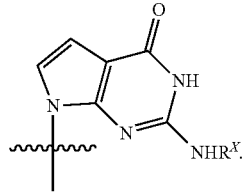

In some embodiments, B is

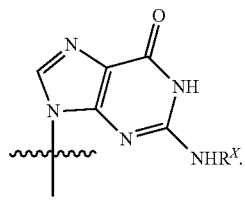

In some embodiments, $R^x$ is hydrogen, $C_1$-$C_6$ alkyl (such as methyl, ethyl, isopropyl, n-butyl, t-butyl), or an amino protecting group. In one embodiment, $R^x$ is methyl. In other embodiments, the hydrogen in —$NHR^x$ is absent, and $R^x$ is a divalent amino protecting group. In some embodiments, $R^x$ is —C(=O)$C_{1-6}$ alkyl. For example, in some embodiments, $R^x$ is —C(=O)$CH_3$ (Ac), —C(=O)$CH_2CH_3$, or —C(=O)CH($CH_3$)$_2$ (iBu). In other embodiments, $R^x$ is —C(=O)-phenyl. In some other embodiments, the hydrogen in —$NHR^x$ is absent, and $R^x$ directed attaches to the nitrogen atom form an amino protecting group such as amidine type protecting group or the phthaloyl type protecting group. In some such embodiments, $R^x$ is N,N,-dimethylformamidine

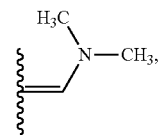 [SMILES: *=CN(C)C]

In some other embodiments, $R^x$ is

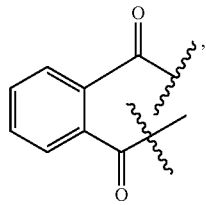 [SMILES: *C(=O)c1ccccc1C(*)=O ; ","]

In some embodiment of the surface bound oligonucleotide or polynucleotide described herein, $R^{Het}$ is optionally substituted 5-10 membered heteroaryl or optionally substituted 5-10 membered heterocyclyl. For example, $R^{Het}$ is optionally substituted 5-10 membered heteroaryl containing one to four heteroatoms selecting from the group consisting of O, N and S. In some further embodiments, $R^{Het}$ is selected from the group consisting of pyridinyl, pyrimidinyl, furanyl, pyrrolyl, thienyl, thiazolyl, isothiazolyl, imidazolyl, pyrazolyl, oxazolyl, isoxazolyl, benzofuranyl, benzoimidazolyl, benzopyrazolyl, benzothiazolyl, benzooxazolyl, indolyl, and quinolinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino ($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, $R^{Het}$ is 4-pyridinyl optionally substituted with one, two or three substituents Q. In some embodiments, $R^{Het}$ is 4-pyridinyl optionally substituted with one, two or three substituents Q, wherein each Q is independently selected from the group consisting of —F, —Cl, —Br, —$CH_3$, —$CH_2CH_3$, —$CF_3$, —$CH_3$, —$OCH_3$, and —$OCH_2CH_3$.

In some other embodiment of the surface bound oligonucleotide or polynucleotide described herein, $R^{Het}$ is optionally substituted 5-10 membered heterocyclyl containing one to four heteroatoms selecting from the group consisting of O, N and S In some such embodiments, $R^{Het}$ is selected from the group consisting of tetrahydofuranyl, tetrahydropyranyl, pyrrolidinyl, piperidinyl, piperazinyl, and morpholinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl. In some embodiments, each Q is independently selected from the group consisting of —F, —Cl, —Br, —$CH_3$, —$CH_2CH_3$, —$CF_3$, —$CH_3$, —$OCH_3$, and —$OCH_2CH_3$.

In some further embodiments of the surface bound oligonucleotide or polynucleotide described herein, the 2' nucleotide residue is selected from the group consisting of:

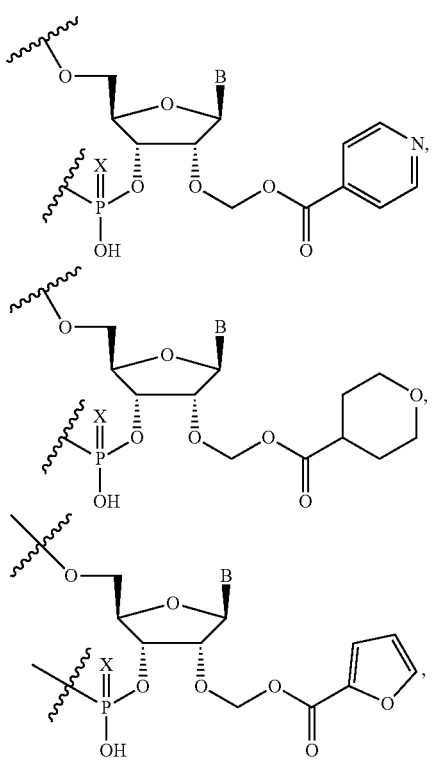

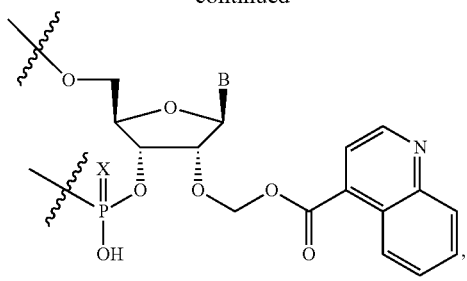

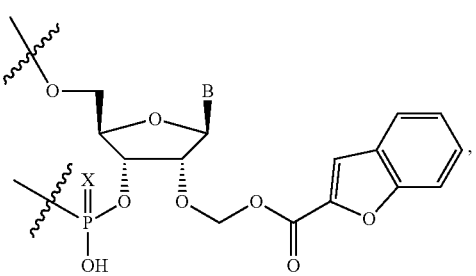

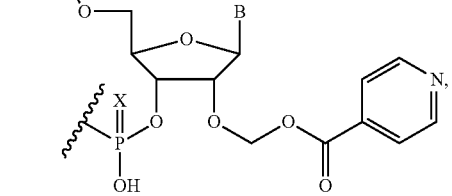

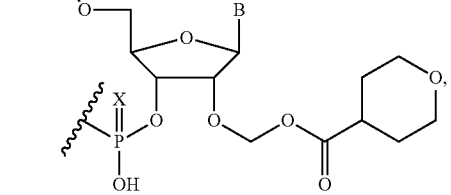

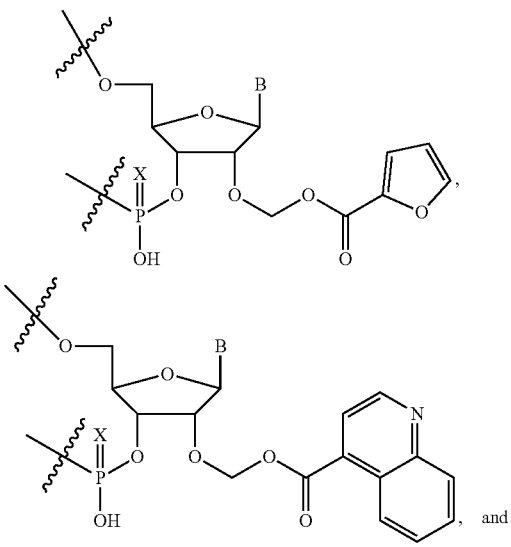

, and

-continued

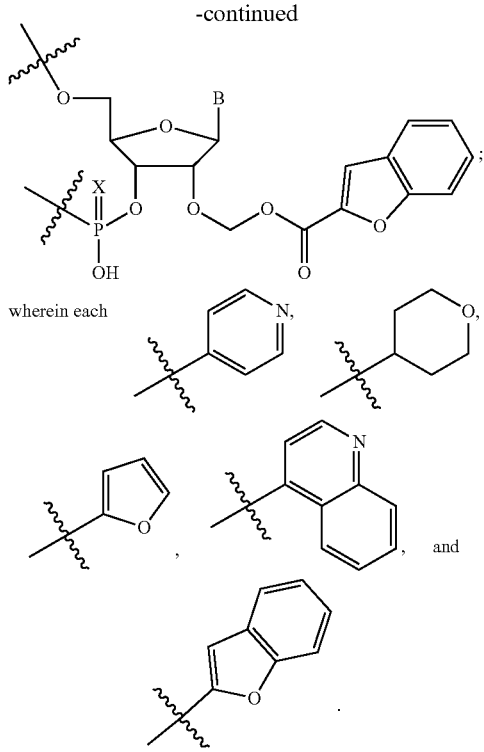

wherein each is optionally substituted with one to three substituent Q, wherein each Q is independently selected from the group consisting of —F, —Cl, —Br, —CH$_3$, —CH$_2$CH$_3$, —CF$_3$, —CH$_3$, —OCH$_3$, and —OCH$_2$CH$_3$; and B is as described. In further embodiments, X is O. In some embodiments, B is

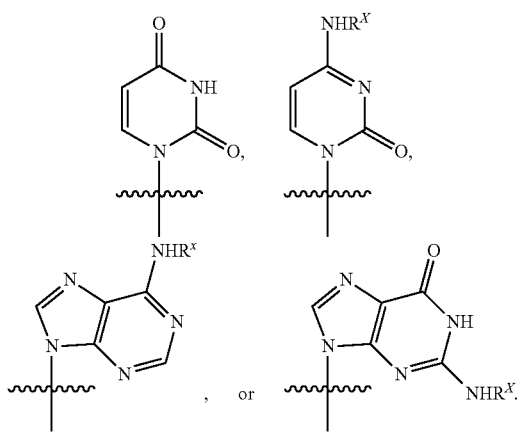

In some further embodiments, R$^x$ is —C(=O)Ph (Bz), —C(=O)CH$_3$ (Ac) or —C(=O)CH(CH$_3$)$_2$ (iBu).

A general description of the oligo synthesis is described below in details.

Step 1: De-Blocking (Detritylation)

The DMTr group is removed with a solution of an acid, such as 2% trichloroacetic acid (TCA) or 3% dichloroacetic acid (DCA), in an inert solvent (dichloromethane or toluene). The orange-colored DMTr cation formed is washed out; the step results in the solid support-bound oligonucleotide precursor bearing a free 5'-terminal hydroxy group.

Step 2: Coupling

A 0.02-0.2M solution of nucleoside phosphoramidite (or a mixture of several phosphoramidites) in acetonitrile is activated by a 0.2-0.7 M solution of an acidic azole catalyst, 1H-tetrazole, 5-ethylthio-1H-tetrazole, 2-benzylthiotetrazole, 4,5-dicyanoimidazole, or a number of similar compounds. The mixing is usually very brief and occurs in fluid lines of oligonucleotide synthesizers (see below) while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The reaction is also highly sensitive to the presence of water, particularly when dilute solutions of phosphoramidites are used, and is commonly carried out in anhydrous acetonitrile. Upon the completion of the coupling, any unbound reagents and by-products are removed by washing.

Step 3: Capping

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'-OH groups (0.1 to 1%) remains unreacted and needs to be permanently blocked from further chain elongation to prevent the formation of oligonucleotides with an internal base deletion commonly referred to as (n−1) shortmers. The unreacted 5'-hydroxy groups are, to a large extent, acetylated by the capping mixture.

Step 4: Oxidation

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). The step of oxidation may be substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. At the end of the chain assembly, the oligonucleotide is released from the solid support and is eluted from the column or the well. The two most often used solid-phase materials are controlled pore glass (CPG) and macroporous polystyrene (MPPS).

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis.

MPPS suitable for oligonucleotide synthesis is a low-swellable, highly cross-linked polystyrene obtained by polymerization of divinylbenzene, styrene, and 4-chloromethylstyrene in the presence of a porogeneous agent. The macroporous chloromethyl MPPS obtained is converted to aminomethyl MPPS.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. Preparation of 2'-O-Protected Phosphoramidite, Succinate and Conjugation to Solid Support

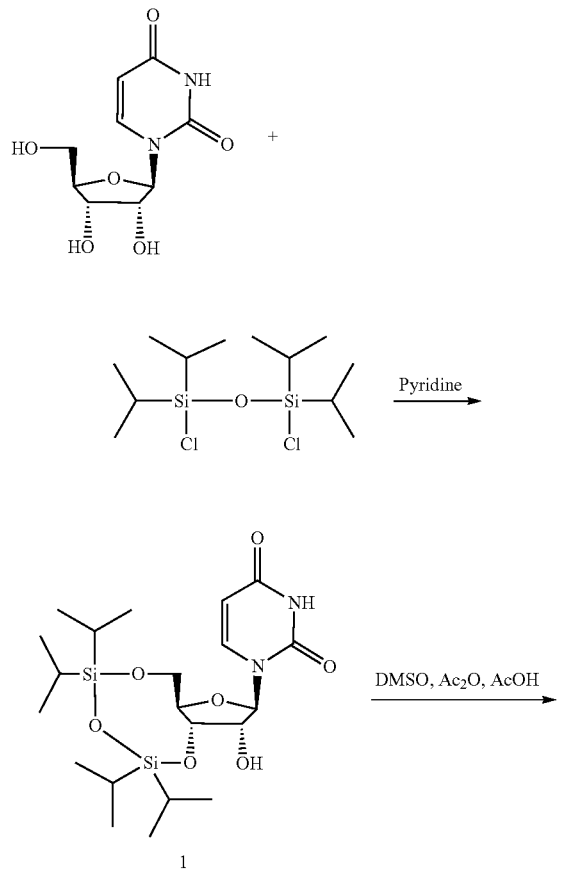

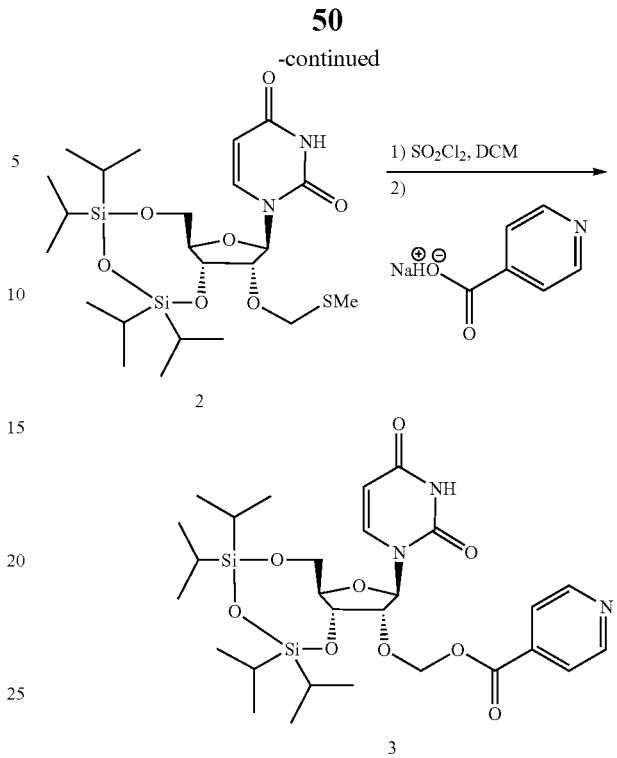

Step 1: Compound 1 was synthesized according to the literature (J. Am. Chem. Soc. 2009, 131, 8496-8502). Uridine (1.0 g, 4.1 mmol) was dissolved in pyridine (10.0 mL) under argon and 1,3-dichloro-1,1,3,3-tetraisopropyldisiloxane (TIPDSiCl$_2$) was then added (1.37 mL, 4.3 mmol). The reaction mixture was stirred at room temperature for 2.5 h and was diluted with dichloromethane (DCM) (10 mL). Brine (10 mL) was then added to the reaction, and the organic phase was separated. The aqueous phase was extracted with dichloromethane (10 mL) two times, and the combined organic phase was dried over Na$_2$SO$_4$, filtered and concentrated to dryness to obtain white foam (crude: 2.35 g). The crude material was used without further purification.

Step 2: Compound 2 was synthesized according to the literature (J. Am. Chem. Soc. 2009, 131, 8496-8502). Compound 1 (4.1 mmol) from step 1 was dissolved in dimethylsulfoxide (DMSO) (7.9 mL) followed by addition of acetic acid (14 mL) and acetic anhydride (13.7 mL). The reaction mixture was heated to 50° C. overnight and cooled to room temperature This solution was poured into 2 L Erlenmeyer flask with vigorous stirring, and a solution of K$_2$CO$_3$ (56 g in 500 mL H$_2$O) was added. The white precipitate was filtered and was dissolved in dichloromethane, dried over magnesium sulfate, filtered and concentrated to dryness. The crude material was purified by flash column chromatography (0 to 50% ethyl acetate in dichloromethane) to obtain pale yellow foam (1.05 g, 46.9% yield). MS: found: [M–H]= 545.5; calc: [M–H]=545.2.

Step 3: Compound 2 (1.05 g, 1.92 mmol) from step 2 was dissolved with 38 mL of dichloromethane under a dry argon environment and is cooled to −10° C. Sulfuryl chloride (0.23 mL) was then added dropwise over 4 minutes. The reaction was stirred at room temperature for 1 hour. The solvent was then removed under reduced pressure to give a yellow foam, which was subsequently dissolved in 9.6 mL of dichloromethane. The sodium salt of isonicotinic acid (4.8 mmol) was then added to the stirring solution followed by the addition of 15-crown-5 (1.1 mmol). The reaction mixture was stirred for 1 hour and then quenched with 50 mL H₂O. The solution was then transferred to a separatory funnel and the organic phase was separated. The aqueous layer was then washed with 3×50 mL of dichloromethane. The organic extracts were combined and dried over magnesium sulfate. After filtration, the solvent was removed under reduced pressure to give yellowish foam. This crude material was then purified by column chromatography (0-8% methanol in dichloromethane) giving Compound 3 as a white foam solid in 45.2% yield. MS: found: [M+H]=622.7; calc: [M+H]= 622.3

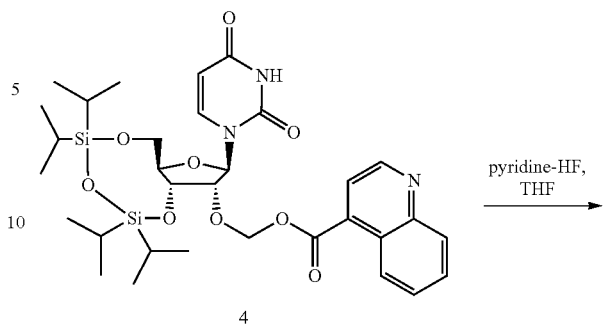

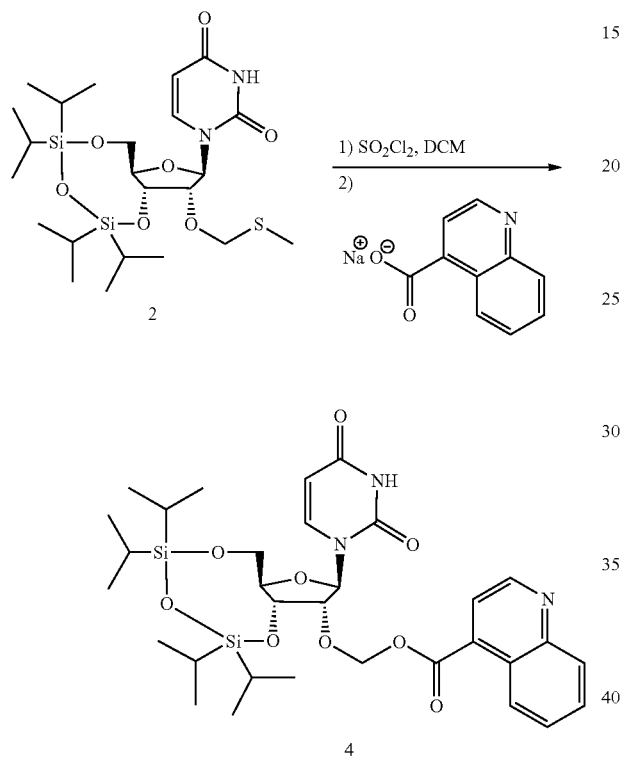

Compound 2 (0.91 g, 1.66 mmol) was dissolved in 33 mL of dichloromethane (DCM) under a dry argon environment and was cooled to −10° C. Sulfuryl chloride (0.20 mL, 2.50 mmol) was then added dropwise over 4 minutes. The reaction was stirred at room temperature for 2 hours. The solvent was then removed under reduced pressure to give a yellow foam. This material was then dissolved in 16 mL of tetrahydrofuran (THF) and sodium salt of 4-quinoline carboxylic acid (0.72 g, 4.15 mmol) was added to the stirring solution followed by the addition of 15-crown-5 (42 µL, 0.21 mmol). The reaction mixture was stirred at room temperature overnight and was quenched with 50 mL of saturated NaHCO₃. The solution was then transferred to a separatory funnel and the organic phase was separated. The aqueous layer was then extracted with ethyl acetate (3×50 mL), and the organic phases were combined, dried over magnesium sulfate. After filtration, the solvent was removed under reduced pressure to give yellowish foam. This crude material was then purified by column chromatography (0-90% ethyl acetate in hexanes) giving Compound 4 as a white solid (0.21 g). MS: found: [M+H]=672.7; calc: [M+H]= 672.3.

Removal of silyl protecting groups: Compound 4 (0.21 g, 0.312 mmol) was dissolved in tetrahydrofuran (THF, 4.0 mL), and pyridine hydrofluoride (70% HF, 0.10 mL, 1.11 mmol) was added. The reaction was stirred at room temperature overnight. Saturated NaHCO₃ (20 mL) was added to the reaction mixture, and this solution was then extracted with ethyl acetate (20 mL) three times. The organic phase was concentrated to dryness under vacuum. This crude material was then purified by column chromatography (0-10% MeOH in DCM) giving Compound 5 as a white solid (60 mg, 44.7% yield). MS: found [M−H]=428.4; calc: [M−H]=428.1.

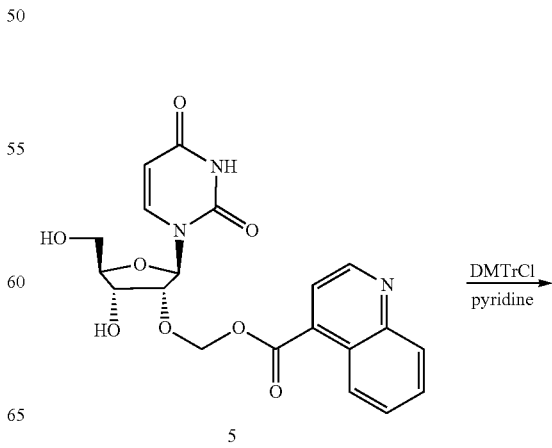

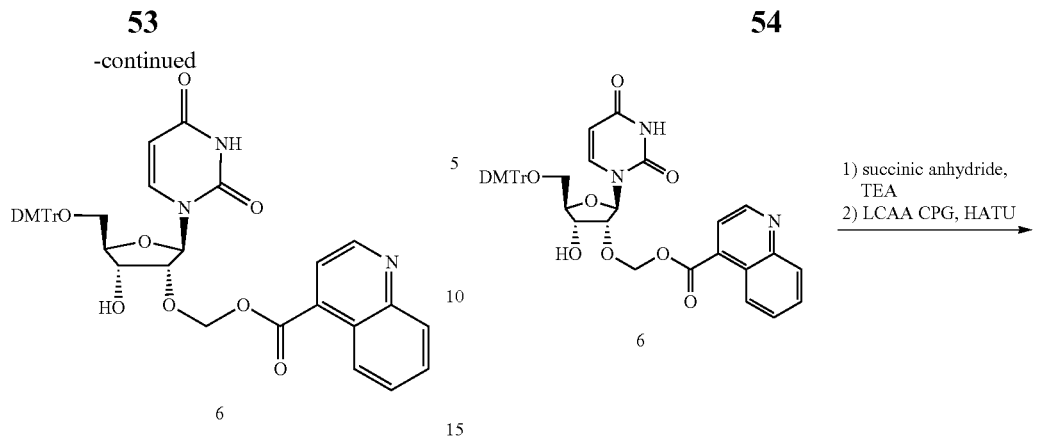

Compound 5 (95 mg, 0.221 mmol) was dissolved in pyridine (1.5 mL) and DMTrCl (85 mg, 0.252 mmol) was then added. The reaction mixture was allowed to stir at r.t. overnight. The reaction was quenched with 5% NaHCO3 solution and extracted with DCM (3×5 mL). The combined organic phases were dried over magnesium sulfate, filtered and concentrated to dryness. The crude material was then purified by column chromatography (0-10% MeOH in DCM) giving Compound 6 as a white solid (24 mg). MS: found [M+H]=732.5; calc: [M+H]=732.3.

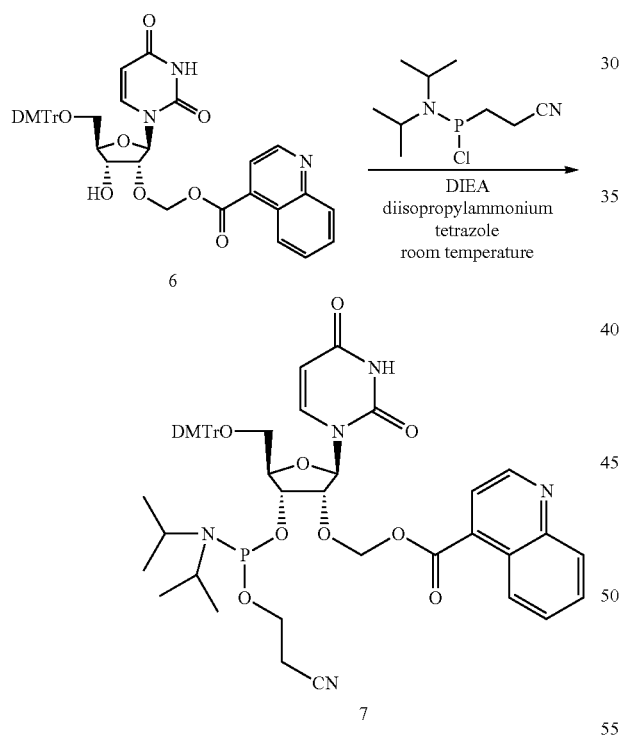

Compound 6 (24 mg, 0.0327 mmol) was dissolved in anhydrous DCM under argon. 2-Cyanoethyl N,N,N',N'-tetraisopropylphosphordiamidite (18.5 µL) and diisopropylammonium tetrazole (1.4 mg) were added. The reaction mixture was stirred at room temperature for 2 hours and was added saturated NaHCO3 (2 mL). DCM (4 mL) was added transferred to separatory funnel. The aqueous phase was separated and extracted with DCM two times (2 mL). The combined organic phase was dried over Na₂SO₄, filtered and concentrated to dryness to afford Compound 7. MS: found [M+H]=932.9; calc: [M+H]=932.4.

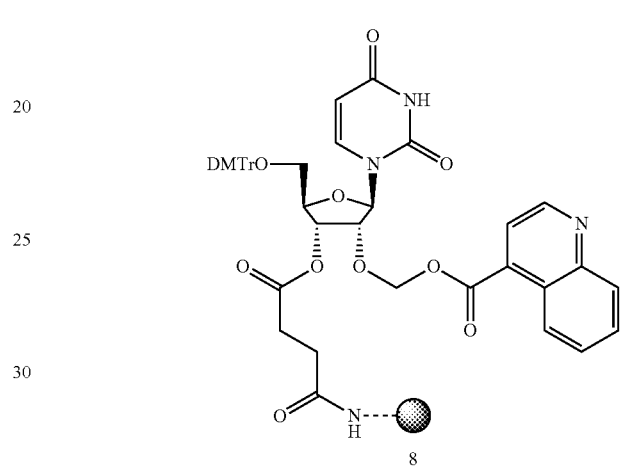

Compound 8. Step 1: In a 50 mL RB flask, Compound 6 (111 mg, (0.152 mmol) was dissolved in 10 mL DCM. Succinic anhydride 22.8 mg (0.228 mmol), TEA 30.7 mg (0.307 mmol were added. At room temperature, the reaction mixture was stirred for 2 hours. Completion of the reaction was confirmed by TLC. This mixture was then poured into saturated NaHCO3 (10 mL), DCM (20 mL) was added, and the organic layer was separated, washed with water, brine and dried over Na₂SO₄. After filtration, the organic layer was concentrated to dryness under vacuum. The crude product was purified by column purification using DCM/MeOH (0% to 10% MeOH). The pure fractions were collected and concentrated to dryness under vacuum to obtain the corresponding succinate (15 mg). MS: found: [M−H]= 830.5; calc: [M−H]=830.3.

Step 2: In a 50 mL RB flask, succinate from above (15 mg, 0.018 mmol) was dissolved in MeCN (5 mL). HATU (6.8 mg, 0.018 mmol) and DIEA 7 mg (0.054 mmol) were added. After 5 min, LCAA CPG (1000 Å, 0.5 g) was added. The reaction mixture was stirred at room temperature for 3 hours. After filtration, this CPG was washed with MeCN (50 mL×3), THF (50 mL×3), and dried under vacuum. Capping A reagent: (THF/acetic anhydride/pyridine 80/10/10 v/v/v, 1.25 mL) and Capping B reagent: (1-methylimidazole/THF, 16/84, v/v, 1.25 mL) were added into the flask, and the mixture was stirred for 2 hours at room temperature. After filtration, the capped CPG was washed with EtOH (50 mL×3), EtOH/Pyridine (10%) (50 mL×3), THF (50 mL×3) and DCM (50 mL×3). This capped CPG bound Compound 8 was then dried under vacuum. Loading was determined by standard DMTr assay by UV-Vis (498 nm) to be 49 µmol/g.

Example 2: Preparation of 2'-O-Protected Adenosine Compound 13 and Conjugation to Solid Support

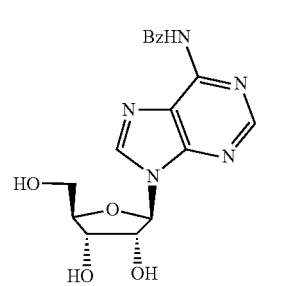

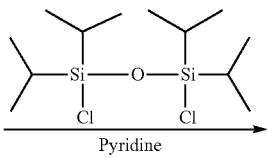

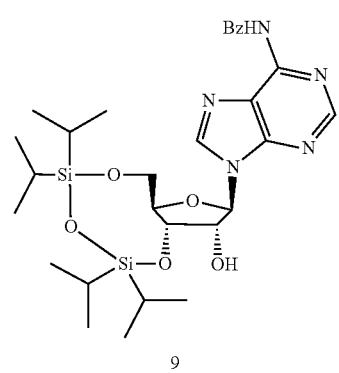

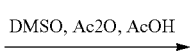

9

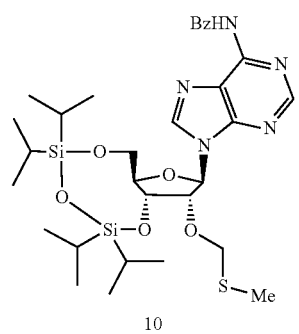

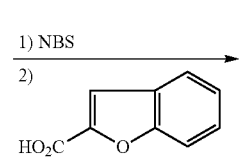

10

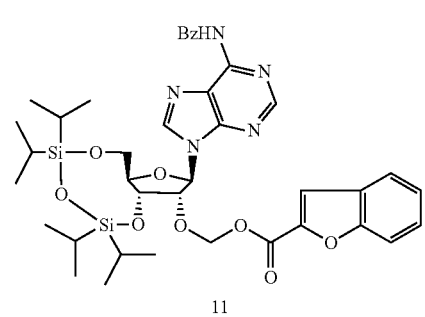

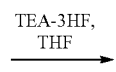

11

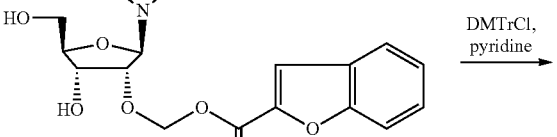

12

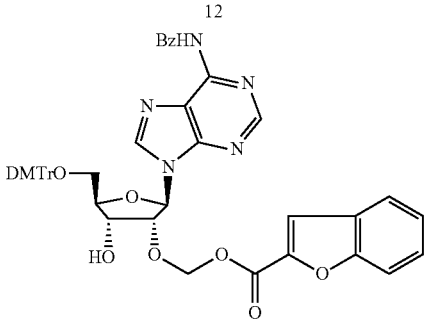

13

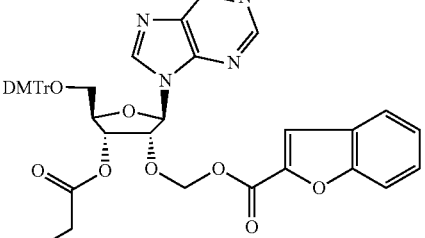

14

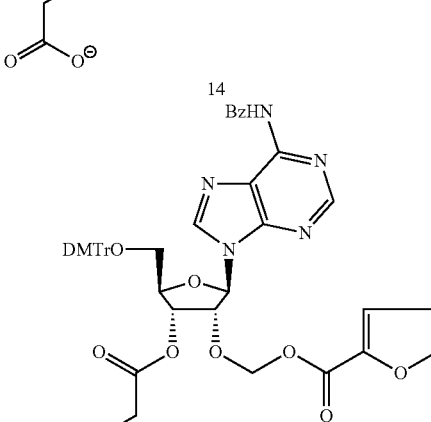

15

Compound 9: N-benzoyl-adenosine (26 g, 70 mmol) was dissolved in pyridine (250 mL), followed by the addition of 1,3-dichloro-1,1,3,3-tetraisopropyldisiloxane (25 g, 80 mmol). The reaction was stirred at room temperature overnight and monitored by TLC. Pyridine was mostly removed and then the residual was redissolved in DCM and washed with brine. The organic layer was separated and dried over sodium sulfate, filtered, and concentrated to dryness. The crude was used directly for next step without further purification (50 g, HPLC purity: 72% with 28% of pyridine). MS: found: [M+H]=614.4; calc: [M+H]=614.3.

Compound 10: A solution of Compound 9 (50 g crude) in DMSO (50 mL) was added acetic anhydride (100 mL) and acetic acid (100 mL). The reaction mixture was heated to 50 degrees Celsius overnight and monitored by LCMS. Upon completion, the reaction was cooled to room temperature, concentrated, and quenched by pouring into saturate potassium carbonate (500 mL). The aqueous phase was extracted with DCM (500 mL) and the organic phase was then washed with brine (500 mL). The organic layer was dried over sodium sulfate, filtered, and concentrated. The residual was subjected to silica column purification using DCM/MeOH (0 to 4% MeOH) to afford Compound 10 (30 g, 64% for 2 steps) as a yellow solid. MS: found: [M+H]=674.6; calc: [M+H]=674.3.

Compound 11: To a solution of Compound 10 (2.2 g, 3.3 mmol) in DMF (15 mL) was added NBS (712 mg, 4.0 mmol). The reaction was stirred for 30 minutes before the addition of benzofuran-2-carboxylic acid (1.62 g, 10 mmol). The reaction was monitored by TLC. Upon completion, the mixture was concentrated, diluted with DCM (20 mL), washed with water (3×20 mL), dried over sodium sulfate, evaporated, and subjected to silica column purification using DCM/MeOH (0 to 4% MeOH) to afford Compound 11 (565 mg, 22%) as a yellow oil. MS: found: [M+H]=788.9; calc: [M+H]=788.31.

Compound 12: Compound 11 (0.565 g, 0.72 mmol) was dissolved in THF (10.2 mL), and TEA-3HF (0.15 mL, 0.90 mmol) was added. The reaction mixture was stirred at r.t. overnight. Upon completion the reaction was quenched with saturated NaHCO$_3$ (5 mL) and volatile was removed under vacuum. DCM (10 mL) was added to extract the aqueous residual, and the organic phase was separated. The aqueous phase was then extracted with DCM (3×10 mL). The combined organic phase was dried over Na$_2$SO$_4$, filtered, and concentrated to dryness. The crude material was purified by flash column chromatograph eluted with DCM and MeOH (0% to 12% MeOH) to afford Compound 12 as an off-white solid (0.20 g, 51.3% yield). MS: found: [M+H]=546.5; calc: [M+H]=546.2.

Compound 13: Compound 12 (0.13 g, 0.24 mmol) was dissolved in pyridine (2.0 mL), and DMTrCl (0.12 g, 0.36 mmol) was added. The reaction mixture was stirred at r.t. overnight. After evaporation of solvent the crude material was purified by flash column chromatograph eluted with DCM/MeOH (0 to 5% MeOH) to obtain Compound 13 as pale-yellow flake (57 mg, 28.2% yield). MS: found: [M+H]= 848.6; calc: [M+H]=848.3.

Compound 14: To a solution of Compound 13 (57 mg, 0.067 mmol) in DCM (1 ml), was added succinic anhydride (10.1 mg, 0.10 mmol) and triethylamine (13.6 mg, 0.136 mmol). The reaction was stirred overnight and monitored by LCMS. Upon completion, the mixture was concentrated and the crude Compound 14 was used directly without further purification. MS: found: [M−H]=946.9; calc: [M−H]=946.29.

Compound 15: Crude Compound 14 from above, 1000 Å LCAA CPG (0.7 g), TBTU (32.4 mg, 1.5 eq.), TEA (13.6 mg, 2 eq.) were dispersed in acetonitrile (3.5 mL). The mixture was placed on a rotovap and stirred for 2 h at 25 degrees Celsius. The mixture was then filtered, and this CPG was washed with acetonitrile (3×3 mL), THF (3×3 mL), and MTBE (3×3 mL), and dried under vacuum to afford uncapped CPG. The uncapped CPG was then dispersed in THF (3.5 mL) with acetic anhydride (0.14 mL), pyridine (0.14 mL) and NMI (0.14 mL). The reaction mixture was placed on a rotovap and stirred for 1 h at 25 degrees Celsius. This capped CPG was then filtered and was washed with pyridine in 10% ethanol (3×3 mL), ethanol (3×3 mL), MeCN (3×3 mL), THF (3×3 mL), and MTBE (3×3 mL), and dried to afford solid support bound Compound 15. Loading was determined by standard DMTr assay by UV-Vis (498 nm) to be 26 μmol/g.

Example 3: Preparation of 2'-O-Protected Adenosine Compound 18 and Conjugation to Solid Support

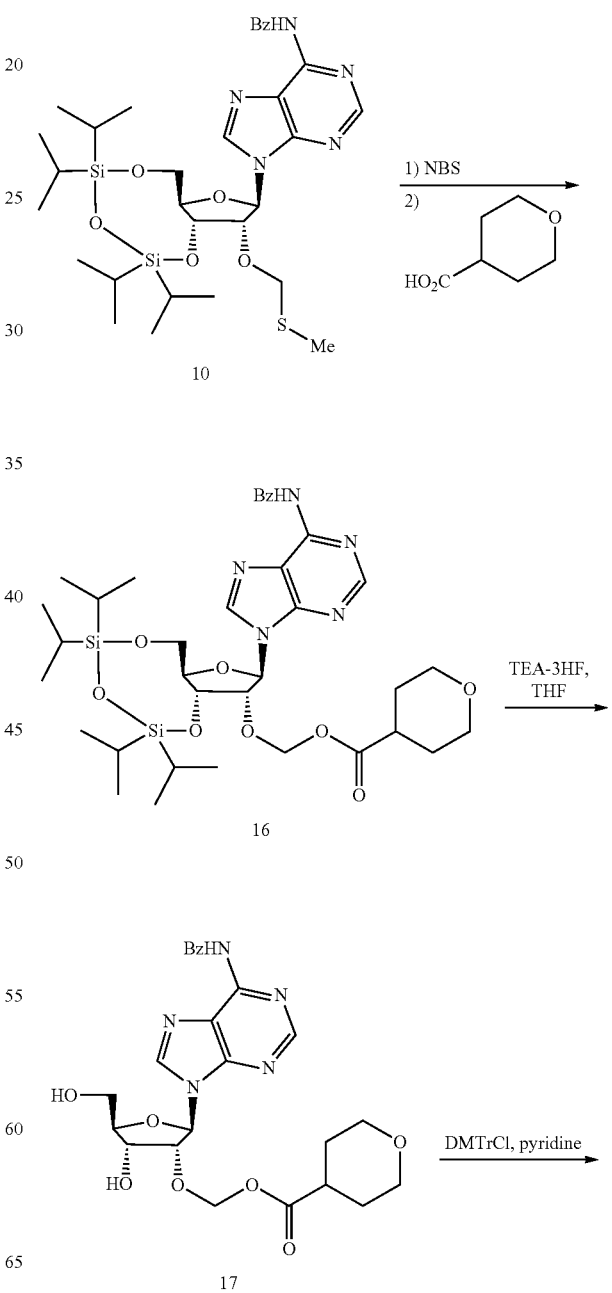

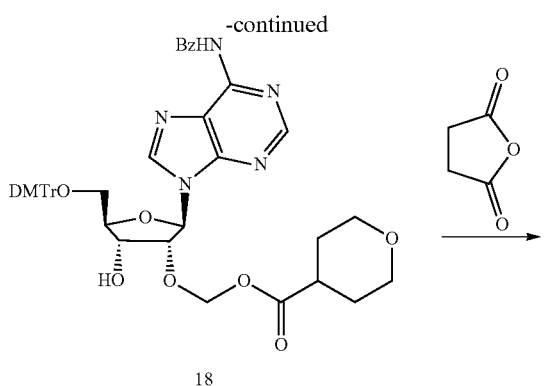

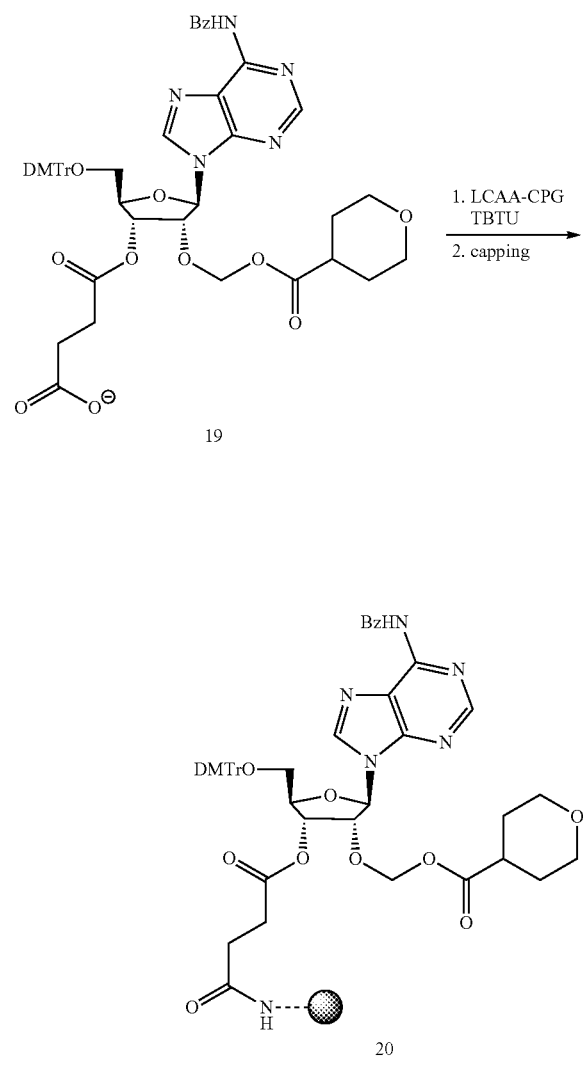

Upon completion, the reaction mixture was concentrated, diluted with DCM (20 mL), washed with water (3×20 mL), dried over sodium sulfate, evaporated, and subjected to silica column purification using DCM/MeOH (0 to 4%) to afford Compound 16 (393 mg, 16% yield) as a yellow oil. MS: found: [M+H]=756.7; calc: [M+H]=756.4.

Compound 17: Compound 16 (0.393 g, 0.52 mmol) was dissolved in THF (7.4 mL), and TEA-3HF (0.11 mL, 0.65 mmol) was added. The reaction mixture was stirred at r.t. overnight. Upon completion the reaction was quenched with saturated $NaHCO_3$ (5 mL) and volatile was removed under vacuum. DCM (10 mL) was added to extract the aqueous residual, and the organic phase was separated. The aqueous phase was then extracted with DCM (3×10 mL). The combined organic phase was dried over $Na_2SO_4$, filtered, and concentrated to dryness. The crude material was purified by flash column chromatograph eluted with DCM and MeOH (0% to 12% MeOH) to afford Compound 17 as an off-white solid (0.10 g, 37% yield). MS: found: [M+H]=514.6; calc: [M+H]=514.2.

Compound 18: Compound 17 (80 mg, 0.16 mmol) was dissolved in pyridine (1.3 mL), and DMTrCl (58 mg, 0.17 mmol) was added. The reaction mixture was stirred at r.t. overnight. After evaporation of solvent and the crude material was purified by flash column chromatograph eluted with DCM/MeOH (0 to 5%) to obtain Compound 18 as pale-yellow oil (30 mg, 23.6% yield). MS: found: [M+H]=816.6; calc: [M+H]=816.3.

Compound 19: To a solution of compound 18 (30 mg, 0.037 mmol) in DCM (1 ml), was added succinic anhydride (5.5 mg, 0.055 mmol) and triethylamine (7.4 mg, 0.074 mmol). The reaction was stirred overnight and monitored by LCMS. Upon completion, the reaction mixture was concentrated, and the crude Compound 19 was used directly without further purification. MS: found: [M−H]=914.9; calc: [M−H]=914.3.

Compound 20: Crude Compound 19 from above, 1000 Å LCAA-CPG (0.3 g), TBTU (6.6 mg, 1.5 eq.), TEA (2.7 mg, 2 eq.) were dispersed in acetonitrile (1.5 mL). The mixture was placed on a rotovap and stirred for 2 h at 25 degrees Celsius. The mixture was then filtered, and this CPG was washed with acetonitrile (3×3 mL), THF (3×3 mL), and MTBE (3×3 mL), and dried to afford uncapped CPG. The uncapped CPG was then dispersed in THF (1.5 mL) with acetic anhydride (60 μL), pyridine (60 μL) and NMI (60 μL). The reaction mixture was placed on a rotovap and stirred for 1 h at 25 degrees Celsius. The reaction mixture was then filtered, and the capped CPG was washed with pyridine in 10% ethanol (3×3 mL), ethanol (3×3 mL), MeCN (3×3 mL), THF (3×3 mL), and MTBE (3×3 mL), and dried to afford solid support bound Compound 20. Loading was determined by standard DMTr assay by UV-Vis (498 nm) to be 14 μmol/g Compound 16: To a solution of Compound 10 (2.2 g, 3.3 mmol) in DMF (15 mL) was added NBS (712 mg, 4.0 mmol). The reaction mixture was stirred for 30 minutes before the addition of tetrahydro-2H-pyran-4-carboxylic acid (1.30 g, 10 mmol). The reaction was monitored by TLC.

Example 4: Preparation of 2'-O-Protected Adenosine Compound 23, Phosphoramidite, and Conjugation to Solid Support
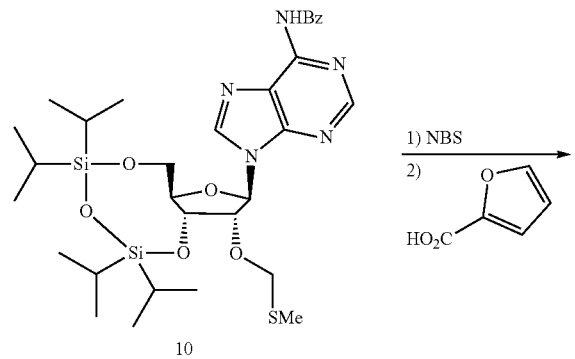
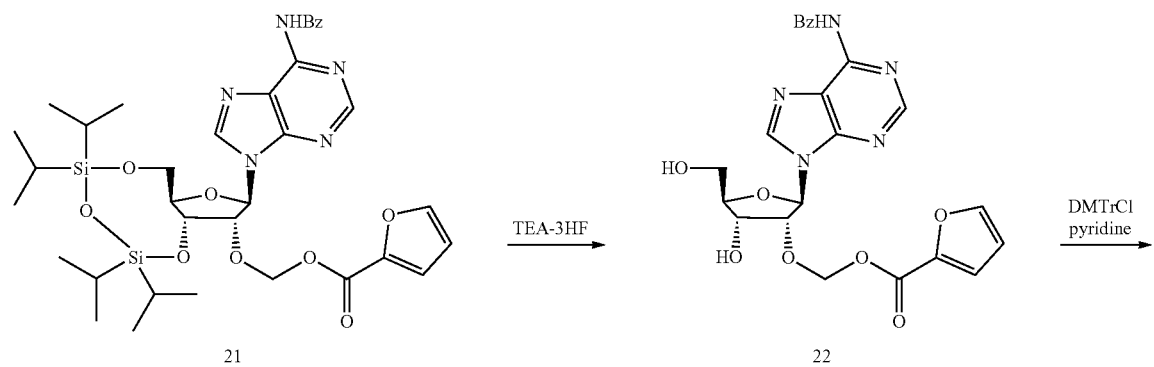
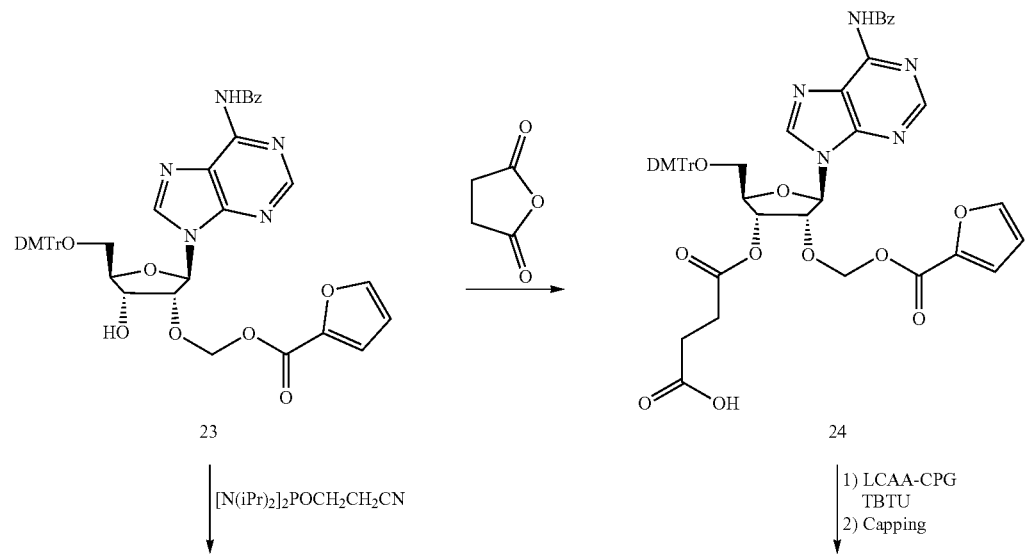

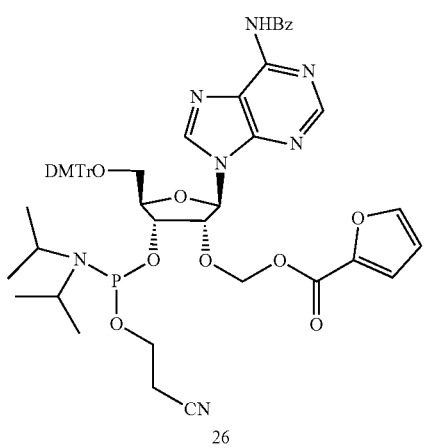

26

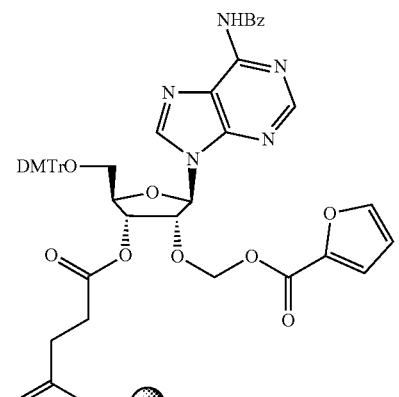

25

Compound 21: To a solution of Compound 10 (6.6 g, 10 mmol) in DMF (50 mL) was added NBS (2.2 g, 12 mmol). The reaction was stirred for 30 minutes before the addition of furan-2-carboxylic acid (3.50 g, 30 mmol). The reaction was monitored by TLC. Upon completion, the reaction mixture was concentrated, diluted with DCM (50 mL), washed with water (3×50 mL), dried over sodium sulfate, concentrated to dryness to afford crude Compound 21 (10 g) which was used directly without further purification. MS: found: [M+H]=738.8; calc: [M+H]=738.3.

Compound 22: To a solution of crude Compound 21 (10 g) in THF (100 mL) was added triethylamine trihydrofluoride (8.25 g, 50 mmol). The reaction was monitored by TLC. Upon completion, the mixture was quenched by sodium bicarbonate, concentrated, diluted with DCM (100 mL), washed with water (3×100 mL), dried over sodium sulfate, evaporated, and subjected to silica column using DCM/MeOH (0 to 8% MeOH) to afford Compound 22 (943 mg, 20% yield for 2 steps) as a pale-yellow solid. MS: found: [M+H]=496.4; calc: [M+H]=496.1.

Compound 23: To a solution of Compound 22 (943 mg, 1.9 mmol) in pyridine (10 mL) was added DMTrCl (773 mg, 2.3 mmol). The reaction was monitored by TLC. Upon completion, the reaction mixture was quenched by methanol, concentrated, and subjected to silica column purification using DCM/MeOH (0 to 10% MeOH) to afford Compound 23 (535 mg, 35% yield) as a white solid. MS: found: [M+H]=798.7; calc: [M+H]=798.3.

Compound 24: To a solution of Compound 23 (120 mg, 0.15 mmol) in DCM (1.0 mL), was added succinic anhydride (22.5 mg, 0.225 mmol) and triethylamine (30 mg, 0.30 mmol). The reaction was stirred at r.t. overnight and monitored by LCMS. Upon completion, the reaction mixture was concentrated, and the crude Compound 24 was used directly without further purification. MS: found: [M−H]=896.9; calc: [M−H]=896.3.

Compound 25: Crude Compound 24, 1000 Å LCAA-CPG (1.5 g), TBTU (72 mg, 1.5 eq.), TEA (30 mg, 2 eq.) were dispersed in acetonitrile (7.5 mL). The reaction mixture was placed on a rotovap and stirred for 2 h at 25 degrees Celsius. The mixture was then filtered, and this CPG was washed with acetonitrile (7.5 mL×3), THF (7.5 mL×3), and MTBE (7.5 mL×3), and dried under vacuum to afford uncapped CPG. The uncapped CPG was then dispersed in THF (7.5 mL) with acetic anhydride (0.3 mL), pyridine (0.3 mL), and NMI (0.3 mL). The reaction mixture was placed on a rotovap and stirred for 1 h at 25 degrees Celsius. The reaction mixture was then filtered, and the capped CPG was washed with pyridine 10% ethanol (7.5×3 mL), ethanol (7.5×3 mL), MeCN (7.5×3 mL), THF (7.5×3 mL), and MTBE (7.5×3 mL), and dried under vacuum to afford solid support bound Compound 25. Loading was determined by standard DMTr assay by UV-Vis (498 nm) to be 19 μmol/g.

Compound 26: Compound 23 (400 mg, 0.5 mmol) and diisopropylammonium tetrazolide (21.4 mg, 0.125 mmol) were dissolved in DCM (4 mL), followed by the addition of 3-((bis(diisopropylamino)phosphanyl)oxy)propanenitrile (301 mg, 1 mmol). The reaction mixture was monitored by LCMS. Upon completion, the reaction was quenched by saturate sodium bicarbonate (3 mL) and washed with saturate sodium bicarbonate (3×3 mL) and brine (3 mL). The organic layer was dried over sodium sulfate, filtered, and concentrated to dryness. The residual was re-dissolved in acetonitrile (3 mL) and washed with heptane (3×3 mL). The acetonitrile layer was concentrated and subjected to silica column purification using TEA/DCM (0.5% to 3% TEA) to afford Compound 26 (260 mg, 52% yield) as a white foam. MS: found: [M+H]=998.5; calc: [M+H]=998.4. $^{31}$PNMR (mixture of diastereomers, DMSO-$d_6$): δ 150.573, 150.245.

Example 5: 2′-O-Protected Uridine Compound 29 and Conjugation to Solid Support

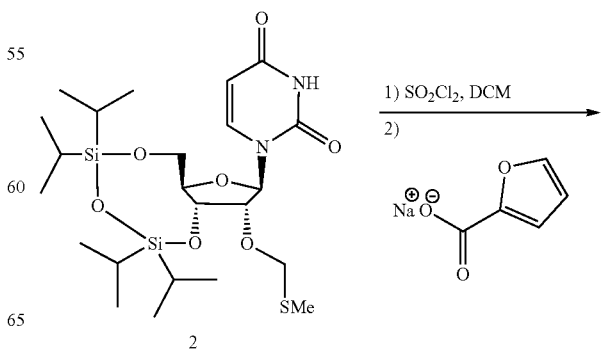

2

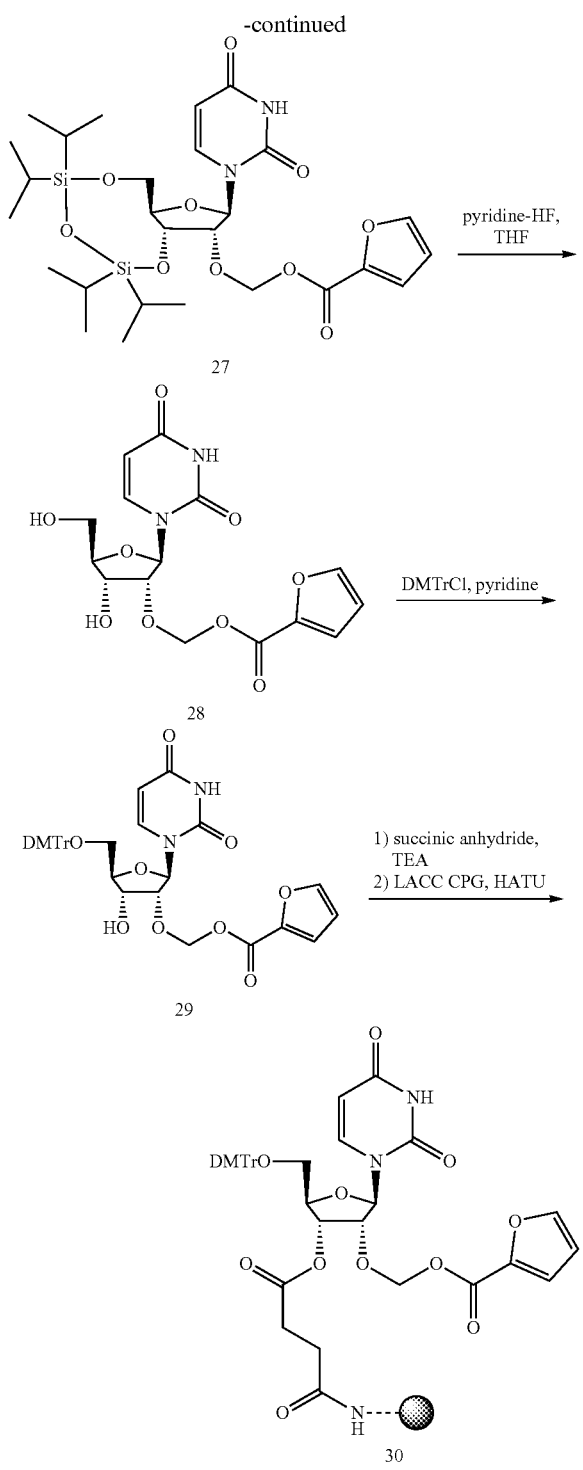

then quenched with H$_2$O (50 mL). The solution was then transferred to a separatory funnel, and the organic phase was separated. The aqueous layer was then washed with dichloromethane (3×50 mL). The combined organic layers were dried over magnesium sulfate. After filtration, the solvent was removed under reduced pressure to give yellowish foam. This crude material was then purified by column chromatography (0-10% methanol in dichloromethane) giving Compound 27 as a white foam solid (1.8 g, 37.3% yield). MS: found: [M−H]=609.5; calc: [M−H]=609.2

Compound 28: Compound 27 (1.8 g, 2.9 mmol) was dissolved in THF (30 mL), and pyridine hydrofluoride (70% HF, 2.8 mL, 17.2 mmol) was added. The reaction was stirred at room temperature overnight. Saturated NaHCO$_3$ (20 mL) was added to the reaction mixture, and this solution was then extracted with ethyl acetate (20 mL×3). The organic phase was concentrated to dryness under vacuum. This crude material was then purified by column chromatography (0-10% MeOH in DCM) giving Compound 28 as a white solid (146 mg, 13.6% yield). MS: found [M−H]=367.4; calc: [M−H]=367.1.

Compound 29: Compound 28 (307 mg, 0.834 mmol) was dissolved in pyridine (25 mL) and DMTrCl (310 mg, 0.917 mmol) was then added. The reaction mixture was allowed to stir at r.t. overnight. The reaction was quenched with 5% NaHCO3 solution and extracted with DCM (3×10 mL). The combined organic phases were dried over magnesium sulfate, filtered and concentrated to dryness. The crude material was then purified by column chromatography (0-10% MeOH in DCM) giving Compound 29 as a white solid (330 mg, 58.7% yield). MS: found [M−H]=699.5; calc: [M−H]=699.2.

Compound 30: Step 1: In a 50 mL RB flask, Compound 29 (330 mg, 0.49 mmol) was dissolved in DCM (30 mL). Succinic anhydride (54 mg, 0.54 mmol), TEA (162 mg, 1.62 mmol) were added. The reaction mixture was stirred at room temperature for 2 hours. Completion of the reaction was confirmed by TLC. This mixture was then poured into saturated NaHCO$_3$ (10 mL), and DCM (20 mL) was added. The organic layer was separated, washed with water, brine and dried over NasSO$_4$. After filtration, the organic layer was concentrated to dryness under vacuum. The crude product was purified by column purification using DCM/MeOH (0% to 10% MeOH). The pure fractions were collected and concentrated to dryness under vacuum to obtain the desired corresponding succinate (80 mg, 21% yield). MS: found: [M+NH$_4$]=788.3; calc: [M+NH$_4$]=788.2.

Step 2: In a 50 mL RB flask, the above succinate (222 mg (0.0288 mmol)) was dissolved in MeCN (5 mL). HATU (11 mg, 0.0288 mmol) and DIEA (11 mg, 0.0864 mmol) were added. After 5 min, The LCAA CPG (1000 Å, 0.8 g) was added. The reaction mixture was stirred at room temperature, for 3 hours. After filtration, this CPG was washed with MeCN (50 mL×3) and THF (50 mL×3), and then dried under vacuum. Capping A reagent: (THF/acetic anhydride/pyridine 80/10/10 v/v/v, 2 mL) and Capping B reagent: (1-methylimidazole/THF, 16/84, v/v, 2 mL) were added into the flask, and the mixture was stirred for 2 hours at room temperature. After filtration, the capped CPG was washed with EtOH (50 mL×3), EtOH/Pyridine (10%) (50 mL×3), THF (50 mL×3) and DCM (50 mL×3). The capped CPG was then dried under vacuum to afford solid support bound Compound 30. Loading was determined by standard DMTr assay by UV-Vis (498 nm) to be 40 μmol/g.

Compound 27: Compound 2 (2.4 g, 4.39 mmol) was dissolved in dichloromethane (60 mL) under a dry argon environment and is cooled to −10° C. Sulfuryl chloride (0.55 mL) was then added dropwise over 4 minutes. The reaction was stirred at room temperature for 1 hour. The solvent was then removed under reduced pressure to give a yellow foam, which was subsequently dissolved in THF (40 mL). The sodium salt of 2-furoic acid (4.39 mmol) was then added to the stirring solution followed by the addition of 15-crown-5 (2.8 mmol). The reaction mixture was stirred for 1 hour and Example 6: Deprotection of 2'-O-Protected Nucleosides

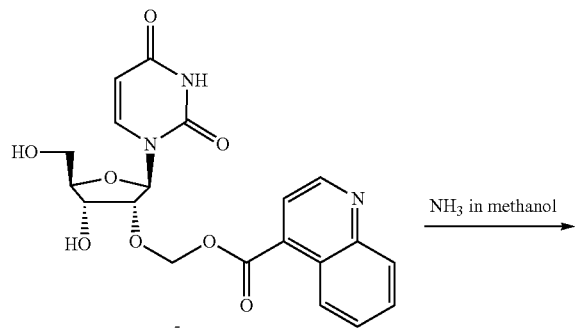

5

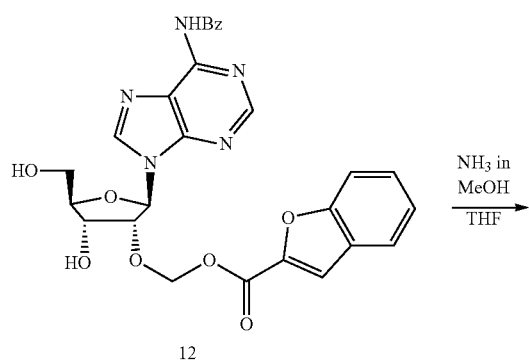

uridine

Compound 5 (10 mg, 0.0233 mmol) was dissolved in THF (0.5 mL), and 2.0 M NH₃ in methanol was added (0.4 mL, 0.89 mmol). The reaction mixture was stirred at r.t. overnight, and TLC confirmed reaction completion. The volatile was removed under vacuum to obtain uridine. MS: found: [M−H]=243.3; calc: [M−H]=243.1.

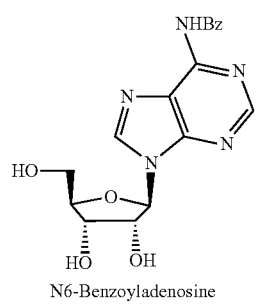

12

Compound 12 (70 mg, 0.13 mmol) was dissolved in THF (2.6 mL), and 2.0 M NH₃ in methanol (2.4 mL) was added. The reaction mixture was stirred at r.t overnight and was monitored by TLC. Upon completion the volatile was remove under vacuum and the residual was dissolved in MeOH (0.5 mL) and MTBE was added for precipitation. The solid was then filtered and dried under vacuum to obtain N6-benzoyladensoine (25.6 mg, 53.9% yield). MS: found: [M+H]=372.1; calc: [M+H]=372.1.

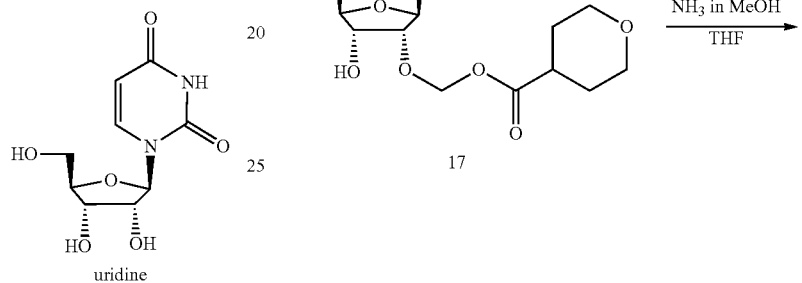

17

N6-Benzoyladenosine

Compound 17 (20 mg, 0.039 mmol) was dissolved in THF (0.78 mL), and 2.0 M NH₃ in methanol (0.74 mL) was added. The reaction mixture was stirred at r.t overnight and was monitored by TLC. Upon completion the volatile was remove under vacuum, and the residual was dissolved in MeOH (0.2 mL) and MTBE was added for precipitation. The solid was then filtered and dried under vacuum to obtain N6-benzoyladensoine (5.4 mg, 37.5% yield). MS: found: [M+H]=372.1; calc: [M+H]=372.1.

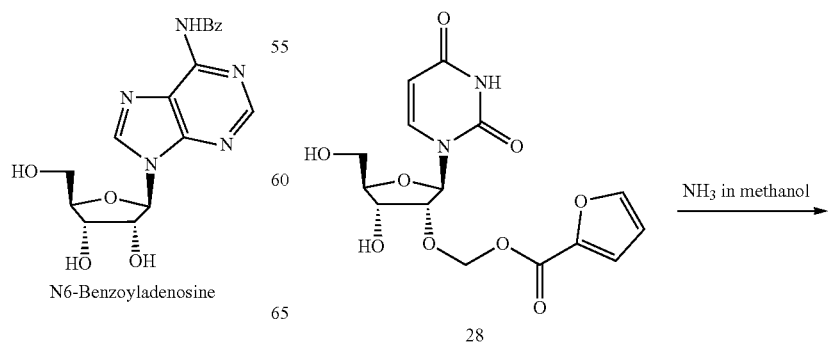

N6-Benzoyladenosine

28

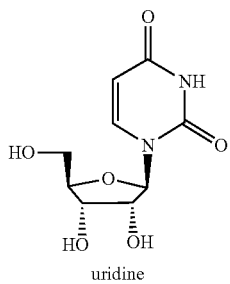
uridine

Compound 28 (3 mg, 0.008 mmol) was dissolved in THF (0.2 mL), and 2.0 M $NH_3$ in methanol was added (0.15 mL). The reaction mixture was stirred at r.t. overnight, and TLC confirmed reaction completion. The volatile was removed under vacuum to obtain uridine. MS: found: [M−H]=243.3; calc: [M−H]=243.1.

Example 7. Preparation of Oligonucleotides

Oligonucleotides were synthesized on a DNA/RNA synthesizer starting with a DMTr-nucleoside-phosphoramidite described herein. The standard synthetic cycle useful in assembling oligonucleotides comprise the steps of: (a) detritylation of the solid phase-bound material; (b) coupling of nucleoside phosphoramidite building block required by the sequence to the solid support-bound material in the presence of coupling agent; (c) capping of unreacted solid support-bound hydroxy groups with a mixture of acetic anhydride and N-methyl imidazole and (d) oxidation of the solid support-bound phosphite triester groups. The cycle appropriate for the assembly of the desired oligonucleotide was repeated as required by the sequence in preparation.

The final release of oligonucleotides from the solid support, deprotection of internucleosidic phosphates, and monosaccharide residues was carried out by treatment under the following standard condition. Upon completion of the deprotection under the conditions above, the liquid phase was collected and evaporated in vacuo to dryness. The residue was dissolved in water (1 mL) and analyzed by reverse-phase HPLC and by ES MS.

To demonstrate the usage of these 2'-O-protected RNA solid supports in DNA/RNA oligonucleotide synthesis, a sequence was designed for trials: 5'-TTTTTTTTTT (SEQ ID NO: 1)-Y-3' (Y represents 2'-O-protected RNA nucleoside conjugated solid support), and it generated the following compounds: T10Y1, T10Y2, T10Y3, T10Y4, and T10Y5.

Oligonucleotides (Compounds T10Y1 through T10Y5) were synthesized by solid-phase phosphoramidite method. A 2'-O-protected RNA conjugated solid support (Y) was packed in an empty column and put into the MerMade 6 synthesizer. The synthetic scale is 0.5-1 µmol. The oligonucleotide synthesis cycle includes the following steps: (1) detritylation with 3% trichloroacetic acid in dichloromethane for 45 second two times, followed by acetonitrile washing; (2) coupling with 0.1 M DMT-dT-CE-Phosphoramidite (5'-O-(4,4'-dimethoxytrityl)-thymidine-3'-cyanoethyl phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 second, followed by acetonitrile washing; and (4) capping with a mixture of acetic anhydride, pyridine, and THF for 45 second, followed by acetonitrile washing. Steps (1)-(4) were repeated 10 times for synthesizing a T10 elongated from the 2'-O-protected RNA conjugated solid support and finished by the final detritylation with acetonitrile washing.

After synthesis, the oligonucleotide-bounded solid supports were treated with a 1:1 mixture of aqueous ammonia hydroxide and methylamine at 55° C. for 2 hr for cleavage and deprotection. The 2'-O-protecting group is also removed at this step. Upon completion, the liquid phase was collected, and heat dried in vacuum. The dried residue was dissolved in water and analyzed by reverse-phase HPLC (Agilent 1260) and LC-MS (Applied Biosystems 4000 Q-Trap). The HPLC gradient was 20-60% B in 20 min, with A: 50 mM triethylammonium acetate in water and B: 80% 50 mM triethylammonium acetate in water and 20% acetonitrile. The retention time (RT), MS calculated, MS found, and full-length product purity (FLP) for each sequence (compounds T10Y1, T10Y2, T10Y3, T10Y4, and T10Y5) were listed in Table 1.

TABLE 1

Usage tests of 2'-O-protected RNA conjugated solid supports

| CPG Compound | Oligo | Sequence after deprotection | RT (min) | FLP % | Mass calculated | Mass found |
|---|---|---|---|---|---|---|
| 2'-O-PG1-A(Bz) CPG (20) | T10Y1 | T10-A | 17.365 | 76.4 | 3310.2 | 3309.8 |
| 2'-O-PG2-A(Bz) CPG (15) | T10Y2 | T10-A | 17.386 | 74.5 | 3310.2 | 3310.6 |
| 2'-O-PG3-A(Bz) CPG (25) | T10Y3 | T10-A | 17.522 | 77.8 | 3310.2 | 3311.3 |
| 2'-O-PG3-U CPG (30) | T10Y4 | T10-U | 18.070 | 70.2 | 3287.2 | 3287.4 |
| 2'-O-PG4-U CPG (8) | T10Y5 | T10-U | 18.034 | 71.5 | 3287.2 | 3287.5 |

PG1 =

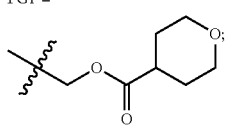

PG2 =

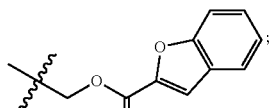

PG3 =

TABLE 1-continued

Usage tests of 2'-O-protected RNA conjugated solid supports

| CPG Compound | Oligo | Sequence after deprotection | RT (min) | FLP % | Mass calculated | Mass found |
|---|---|---|---|---|---|---|

PG4 = 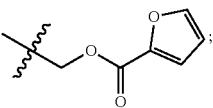

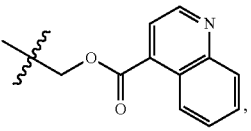 [SMILES: *COC(=O)c1ccnc2ccccc12], where the squiggly line indicates the attachment point to the 2'-oxygen of the ribonucleoside.

While the present application has been described with reference to the specific embodiments thereof, it should be understood by those skilled in the art that various changes may be made, and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A compound of Formula (I):

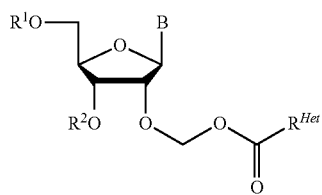

(I)

or a pharmaceutically acceptable salt thereof, wherein
$R^1$ is hydrogen or a hydroxy protecting group;
$R^2$ is hydrogen, a hydroxy protecting group, —C(=O)CH$_2$CH$_2$C(=O)R$^3$, or —P(OR$^4$)NR$^5$R$^6$;
alternatively, $R^1$ and $R^2$ are joined together to form a 6-10 membered heterocyclic ring;
$R^{Het}$ is optionally substituted 5-10 membered heteroaryl or optionally substituted 5-10 membered heterocyclyl;
$R^3$ is hydroxy, —OR$^7$ or —NR$^8$R$^9$;
each of $R^4$, $R^5$ and $R^6$ is independently H, unsubstituted C$_1$-C$_6$ alkyl, or substituted C$_1$-C$_6$ alkyl;

$R^7$ is unsubstituted C$_1$-C$_6$ alkyl, substituted C$_1$-C$_6$ alkyl, or a hydroxy protecting group;
each of $R^8$ and $R^9$ is independently H, unsubstituted or substituted C$_{1-6}$ alkyl, or an amino protecting group; and
B is a natural nucleobase, a modified natural nucleobase, or an unnatural nucleobase.

2. The compound of claim 1, wherein $R^1$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

3. The compound of claim 1, wherein $R^1$ is bis(4-methoxyphenyl)phenylmethyl.

4. The compound of claim 1, wherein $R^1$ is hydrogen.

5. The compound of claim 1, wherein $R^2$ is H.

6. The compound of claim 1, where $R^2$ is —P(OR$^4$)NR$^5$R$^6$, wherein:
$R^4$ is substituted C$_1$-C$_6$ alkyl; and
$R^5$ and $R^6$ are each independently unsubstituted C$_1$-C$_6$ alkyl.

7. The compound of claim 6, wherein R² is

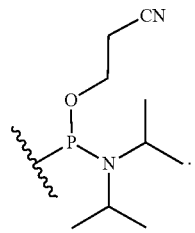

8. The compound of claim 1, wherein R¹ and R² are joined together to form a 7 membered heterocyclic ring containing oxygen and silicon atoms.

9. The compound of claim 8, wherein the compound of Formula (I) is also represented by Formula (Ia):

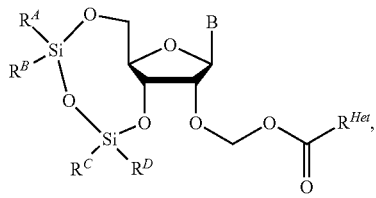

(Ia)

or a pharmaceutically acceptable salt thereof, wherein each of $R^A$, $R^B$, $R^C$, and $R^D$ is independently H, unsubstituted $C_1$-$C_6$ alkyl, or substituted $C_1$-$C_6$ alkyl.

10. The compound of claim 9, wherein each of $R^A$, $R^B$, $R^C$, and $R^D$ is isopropyl.

11. The compound of claim 1, wherein $R^{Het}$ is optionally substituted 5-10 membered heteroaryl containing one to four heteroatoms selecting from the group consisting of O, N and S.

12. The compound of claim 11, wherein $R^{Het}$ is selected from the group consisting of pyridinyl, pyrimidinyl, furanyl, pyrrolyl, thienyl, thiazolyl, isothiazolyl, imidazolyl, pyrazolyl, oxazolyl, isoxazolyl, benzofuranyl, benzoimidazolyl, benzopyrazolyl, benzothiazolyl, benzooxazolyl, indolyl, and quinolinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino ($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$alkyl.

13. The compound of claim 12, wherein each Q is independently selected from the group consisting of —F, —Cl, —Br, —CH₃, —CH₂CH₃, —CF₃, —CH₃, —OCH₃, and —OCH₂CH₃.

14. The compound of claim 1, wherein $R^{Het}$ is optionally substituted 5-10 membered heterocyclyl containing one to four heteroatoms selecting from the group consisting of O, N and S.

15. The compound of claim 14, wherein $R^{Het}$ is selected from the group consisting of tetrahydrofuranyl, tetrahydropyranyl, pyrrolidinyl, piperidinyl, piperazinyl, and morpholinyl, each optionally substituted with one, two or three substituents Q; wherein each Q is independently selected from the group consisting of halo, cyano, hydroxy, amino, $C_1$-$C_6$ alkyl, $C_1$-$C_6$ haloalkyl, hydroxy($C_1$-$C_6$ alkyl), amino ($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl and —O($C_1$-$C_6$ alkoxy)$C_1$-$C_6$ alkyl.

16. The compound of claim 1, wherein B is:

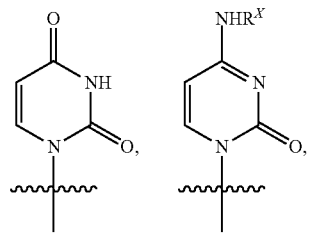

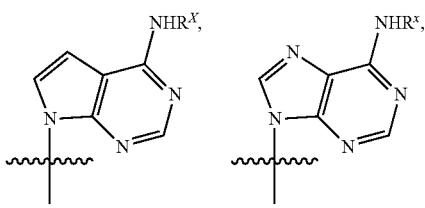

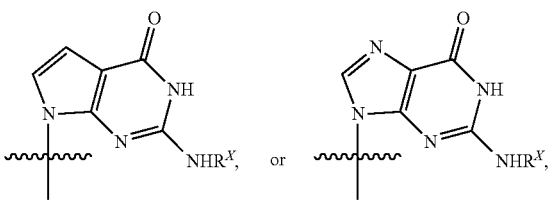

wherein $R^x$ is hydrogen, unsubstituted or substituted $C_1$-$C_6$ alkyl, or an amino protecting group, or the hydrogen in —NHR$^x$ is absent and R$^x$ is a divalent amino protecting group.

17. The compound of claim 16, wherein R$^x$ is —C(=O)Ph (Bz), —C(=O)CH₃ (Ac) or —C(=O)CH(CH₃)₂ (iBu), or the hydrogen in —NHR$^x$ is absent and R$^x$ is

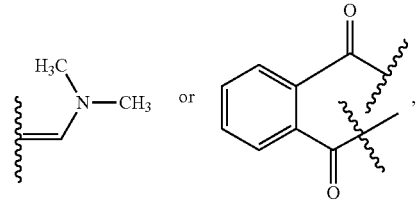

18. The compound of claim 1, selected from the group consisting of:

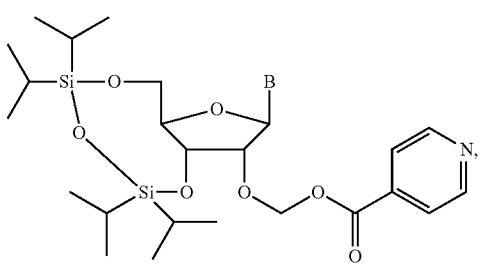

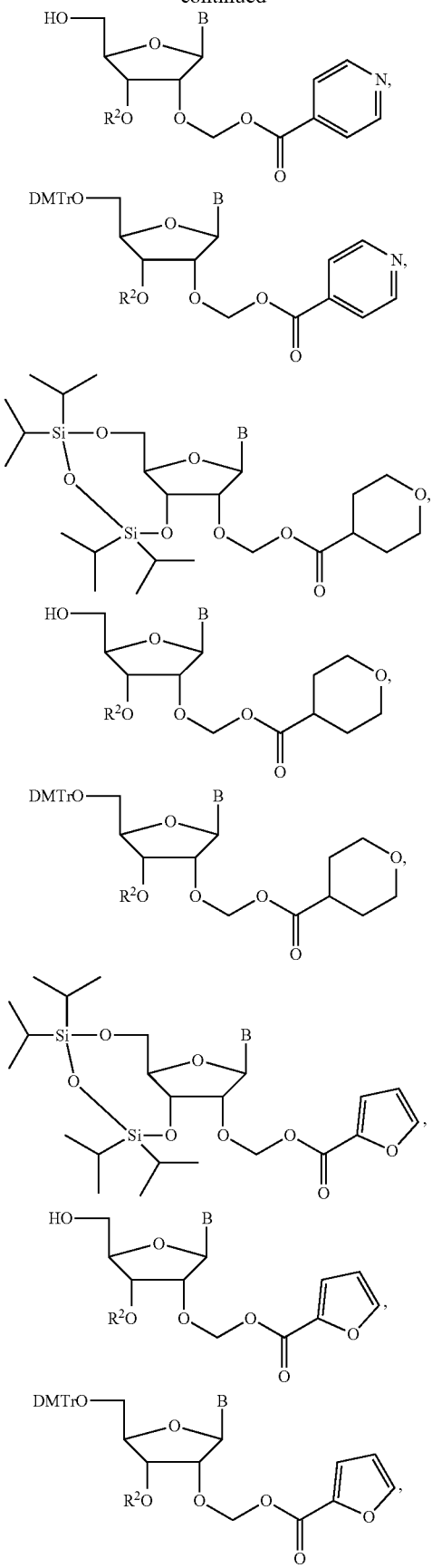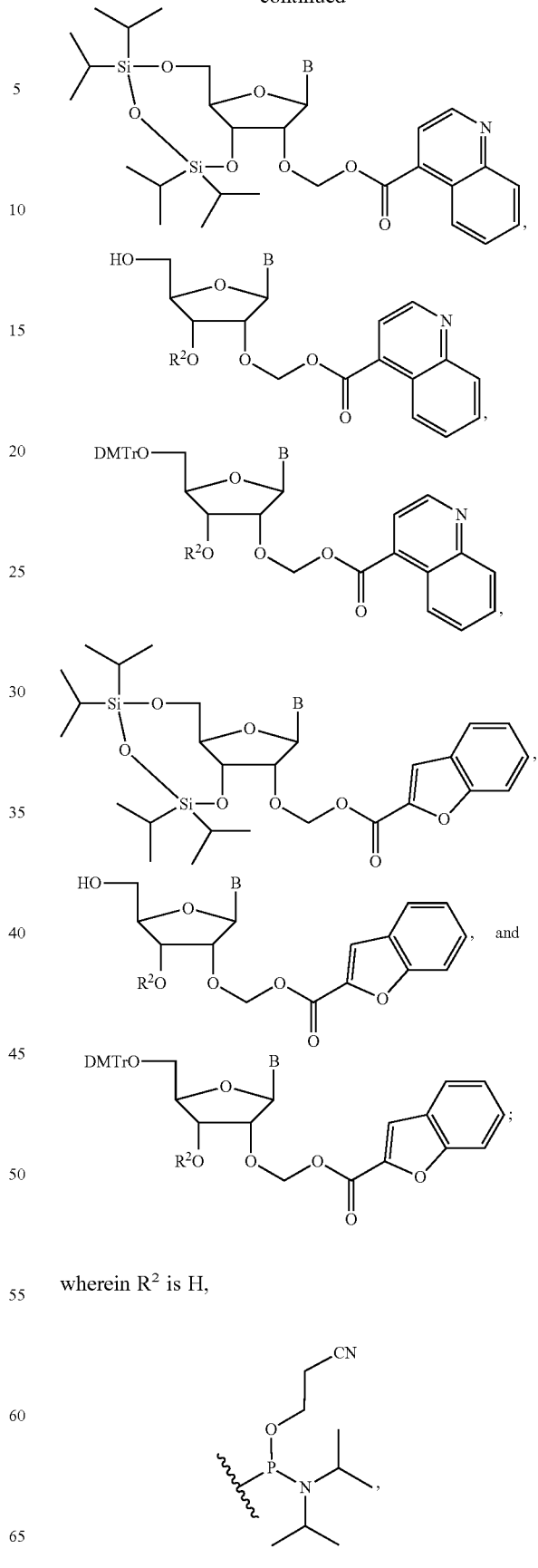
wherein $R^2$ is H,

—C(=O)CH$_2$CH$_2$C(=O)OH or —C(=O)CH$_2$CH$_2$C(=O)NH$_2$;

each

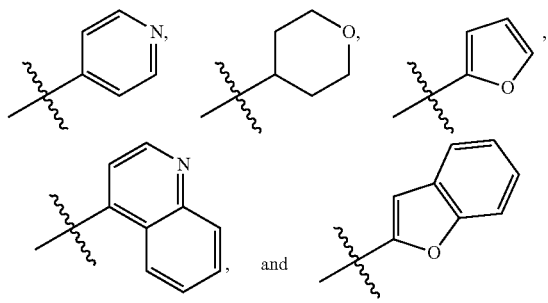

and is optionally substituted with one to three substituent Q, and wherein each Q is independently selected from the group consisting of —F, —Cl, —Br, —CH$_3$, —CH$_2$CH$_3$, —CF$_3$, —CH$_3$, —OCH$_3$, and —OCH$_2$CH$_3$.

19. The compound of claim 18, wherein B is

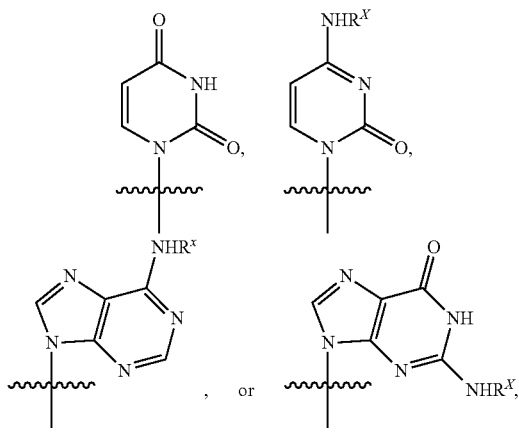

wherein R$^x$ is —C(=O)Ph (Bz), —C(=O)CH$_3$ (Ac) or —C(=O)CH(CH$_3$)$_2$ (iBu).

20. A method of preparing a synthetic oligonucleotide, comprising reacting a compound of claim 1, with an oligonucleotide.

21. An oligonucleotide or polynucleotide prepared by the method of claim 20.

22. A method of deprotecting an oligonucleotide or polynucleotide comprising at least one 2' protected nucleotide residue comprising the structure of Formula (II):

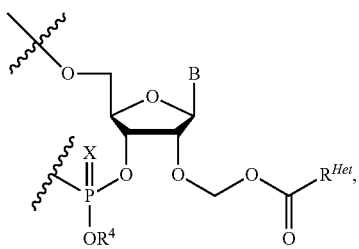

wherein
X is O or S;
R$^4$ is H, unsubstituted C$_1$-C$_6$ alkyl or substituted C$_1$-C$_6$ alkyl;
B is a natural nucleobase, a modified natural nucleobase, or an unnatural nucleobase; and
R$^{Het}$ is optionally substituted 5-10 membered heteroaryl or optionally substituted 5-10 membered heterocyclyl;

the method comprising:
contacting the oligonucleotide or polynucleotide with a composition comprising an amine or ammonia to deprotect the 2' protected nucleotide residue.

23. A solid support bound oligonucleotide or polynucleotide comprising at least one 2' protected nucleotide residue comprising the structure of Formula (II):

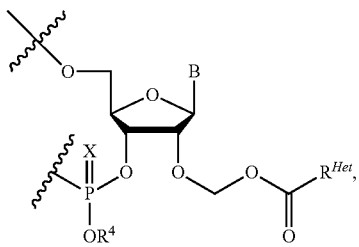

wherein
X is O or S;
R$^4$ is H, unsubstituted C$_1$-C$_6$ alkyl or substituted C$_1$-C$_6$ alkyl;
B is a natural nucleobase, a modified natural nucleobase, or an unnatural nucleobase; and
R$^{Het}$ is optionally substituted 5-10 membered heteroaryl or optionally substituted 5-10 membered heterocyclyl.

* * * * *